(12) United States Patent
Park et al.

(10) Patent No.: US 11,951,449 B2
(45) Date of Patent: Apr. 9, 2024

(54) METHOD FOR PREPARING ORGANIC-INORGANIC HYBRID MICROCAPSULE

(71) Applicants: LG HOUSEHOLD & HEALTH CARE LTD., Seoul (KR); LG CHEM, LTD., Seoul (KR)

(72) Inventors: Nojin Park, Daejeon (KR); Woo Sun Shim, Daejeon (KR); Junseok Yeom, Daejeon (KR); Jee Seon Kim, Daejeon (KR); Sangryeo Lee, Daejeon (KR); Chanjoong Kim, Daejeon (KR); Minchae Kim, Daejeon (KR); Myeongho Kim, Daejeon (KR)

(73) Assignees: LG HOUSEHOLD & HEALTH CARE LTD., Seoul (KR); LG CHEM, LTD., Seoul (KR)

(*) Notice: Subject to any disclaimer, the term of this patent is extended or adjusted under 35 U.S.C. 154(b) by 628 days.

(21) Appl. No.: 17/257,159

(22) PCT Filed: Jul. 2, 2019

(86) PCT No.: PCT/KR2019/008068
§ 371 (c)(1),
(2) Date: Dec. 30, 2020

(87) PCT Pub. No.: WO2020/009439
PCT Pub. Date: Jan. 9, 2020

(65) Prior Publication Data
US 2021/0138423 A1 May 13, 2021

(30) Foreign Application Priority Data

Jul. 3, 2018 (KR) .................. 10-2018-0077239
Jul. 3, 2018 (KR) .................. 10-2018-0077240

(51) Int. Cl.
| | | |
|---|---|---|
| B01J 13/16 | (2006.01) |
| A61K 9/50 | (2006.01) |
| B01J 35/23 | (2024.01) |
| C09B 67/02 | (2006.01) |
| C09K 15/02 | (2006.01) |
| C09K 15/06 | (2006.01) |
| C09K 15/18 | (2006.01) |
| C09K 15/20 | (2006.01) |
| C11D 3/50 | (2006.01) |

(52) U.S. Cl.
CPC ............ *B01J 13/16* (2013.01); *A61K 9/5031* (2013.01); *B01J 35/23* (2024.01); *C09B 67/0097* (2013.01); *C09K 15/02* (2013.01); *C09K 15/06* (2013.01); *C09K 15/18* (2013.01); *C09K 15/20* (2013.01); *C11D 3/505* (2013.01); *C11D 2111/12* (2024.01)

(58) Field of Classification Search
CPC ........ B01J 13/16; B01J 35/0013; C11D 3/505
See application file for complete search history.

(56) References Cited

U.S. PATENT DOCUMENTS

| | | | |
|---|---|---|---|
| 5,804,298 A | 9/1998 | Moy | |
| 10,059,907 B2 | 8/2018 | Ribaut et al. | |
| 10,526,567 B2* | 1/2020 | Struillou | A61K 8/022 |
| 2011/0204533 A1 | 8/2011 | Winchester et al. | |
| 2014/0127309 A1 | 5/2014 | Drake et al. | |
| 2015/0104545 A1 | 4/2015 | Dardelle et al. | |
| 2015/0231588 A1 | 8/2015 | Moore et al. | |
| 2016/0158121 A1* | 6/2016 | Lei | C11D 17/0039 424/70.17 |
| 2016/0354749 A1 | 12/2016 | Wu et al. | |
| 2018/0057772 A1* | 3/2018 | Saveyn | C11D 3/001 |
| 2019/0255502 A1 | 8/2019 | Wu et al. | |

FOREIGN PATENT DOCUMENTS

| | | |
|---|---|---|
| CN | 1742707 A | 3/2006 |
| CN | 102985175 A | 3/2013 |
| JP | 2004-216241 A | 8/2004 |
| JP | 2015-517554 A | 6/2015 |
| JP | 2016-530982 A | 10/2016 |
| JP | 2017-503643 a | 2/2017 |
| KR | 10-2007-0049378 A | 5/2007 |
| KR | 10-2014-0031364 A | 3/2014 |
| KR | 10-2016-0137820 A | 12/2016 |

(Continued)

OTHER PUBLICATIONS

Extended European Search Report for European Application No. 19830922.1, dated Jun. 18, 2021.
Jagtap et al., "Improved performance of microcapsules with polymer nanocomposite wall: Preparation and characterization," Polymer, vol. 83, 2016 (Available online Dec. 15, 2015), pp. 27-33.
Park et al., "Magnetic nanoparticle-embedded PCM nanocapsules based on paraffin core and polyurea shell," Colloids and Surfaces A: Physicochem Eng. Aspects, vol. 450, 2014 (Available online Mar. 12, 2014), pp. 46-51.
International Search Report issued in PCT/KR2019/008068 (PCT/ISA/210), dated Oct. 18, 2019.

(Continued)

*Primary Examiner* — Andrew S Rosenthal
(74) *Attorney, Agent, or Firm* — Birch, Stewart, Kolasch & Birch, LLP

(57) ABSTRACT

The present disclosure relates to a method for preparing a biodegradable and eco-friendly organic-inorganic hybrid microcapsule having few toxic substances with high versatility and economical efficiency by using a pickering emulsion method with a specific outer wall reinforcing material, a reactive material, and inorganic nanoparticles, and allowing polymerization of the outer wall reinforcing material and the reactive material to proceed at the interface. Specifically, the organic-inorganic hybrid microcapsule can stably support an active ingredient and then effectively express its activity by pressure, and exhibit a characteristic of gradually releasing the active ingredient at room temperature.

15 Claims, 4 Drawing Sheets

(56) References Cited

FOREIGN PATENT DOCUMENTS

WO    WO2018/091705 A1    6/2015
WO    WO-2015091705 A1 *    6/2015    ............. A61K 8/042
WO    WO2018/054718 A1    3/2018

OTHER PUBLICATIONS

"Preparation and Properties of Biodegradable Polysaccharide Nanocapsules," Oct. 13, 2005, p. 655 (2 pages total), with English translation.
Rui et al., "Research Progress on Capsule Wall Materials Used for Drug Microcapsule," Mar. 31, 2012, pp. 28-37 (11 pages total), with English abstract.

* cited by examiner

[FIG. 1]
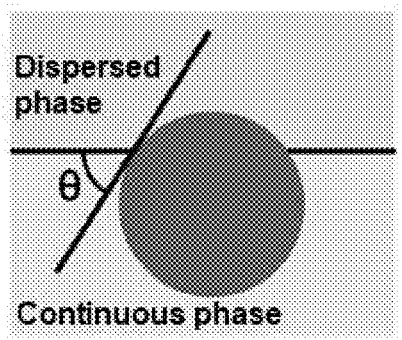
[FIG. 2]
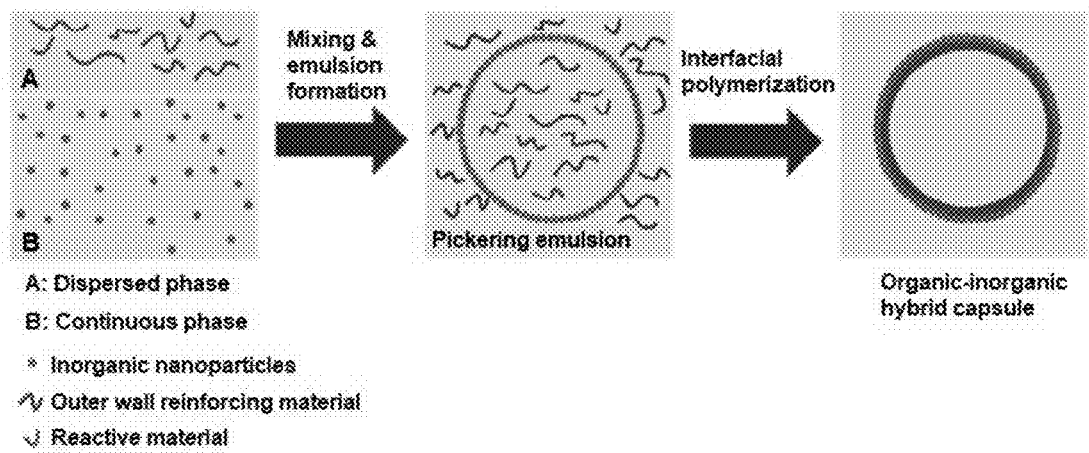

[FIG. 3]
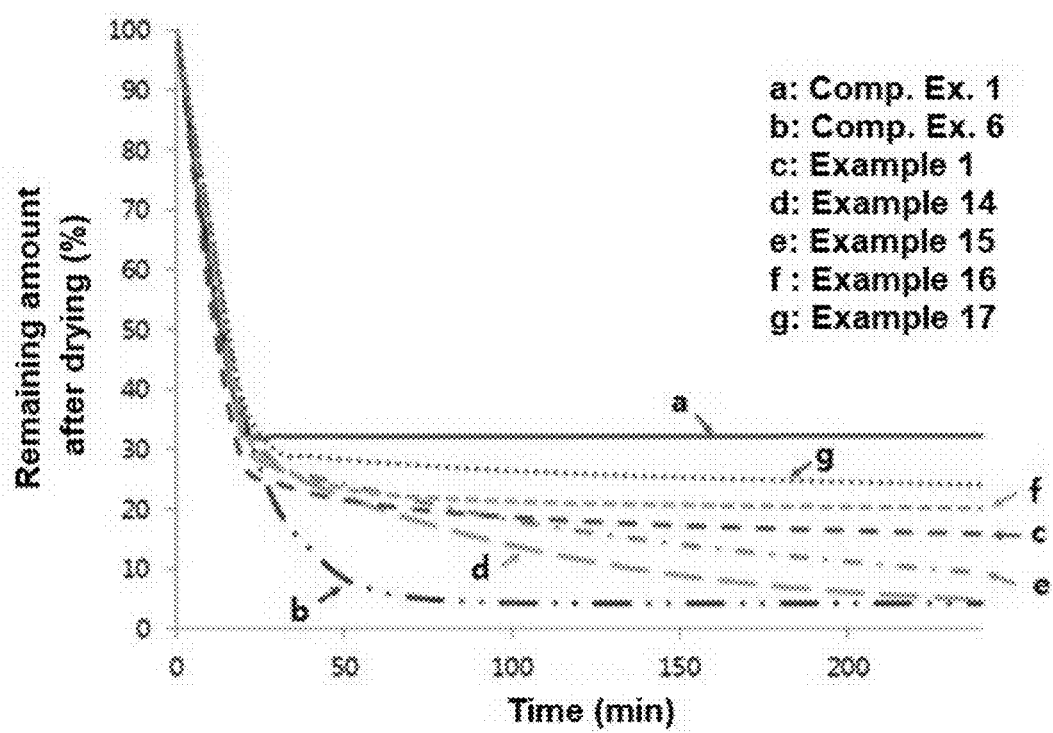

[FIG. 4]
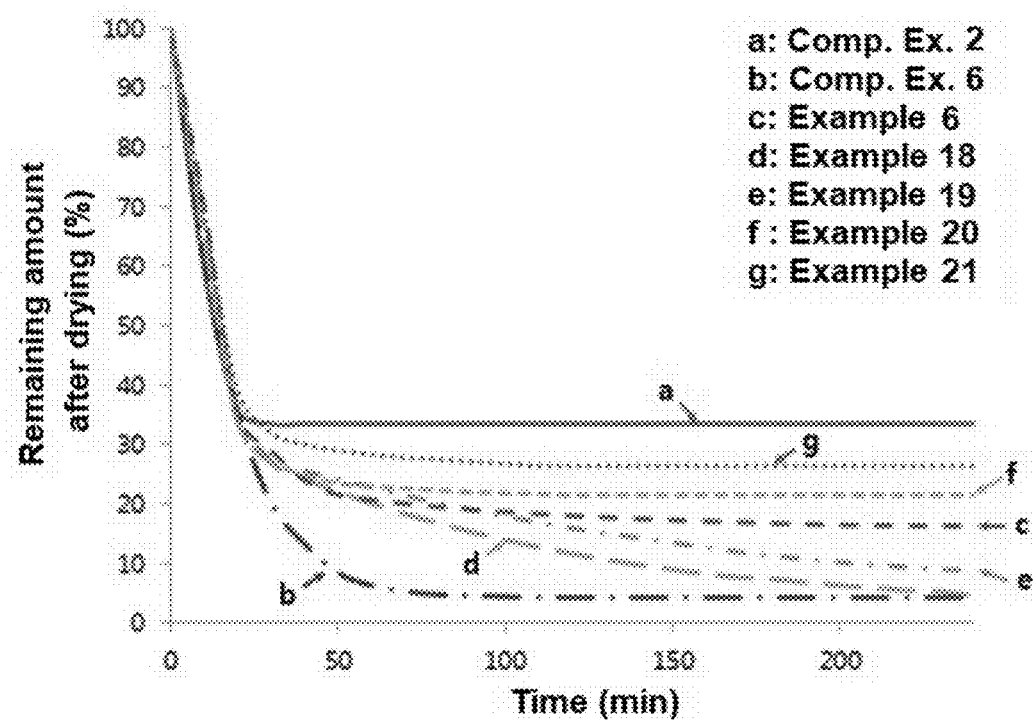

[FIG. 5]
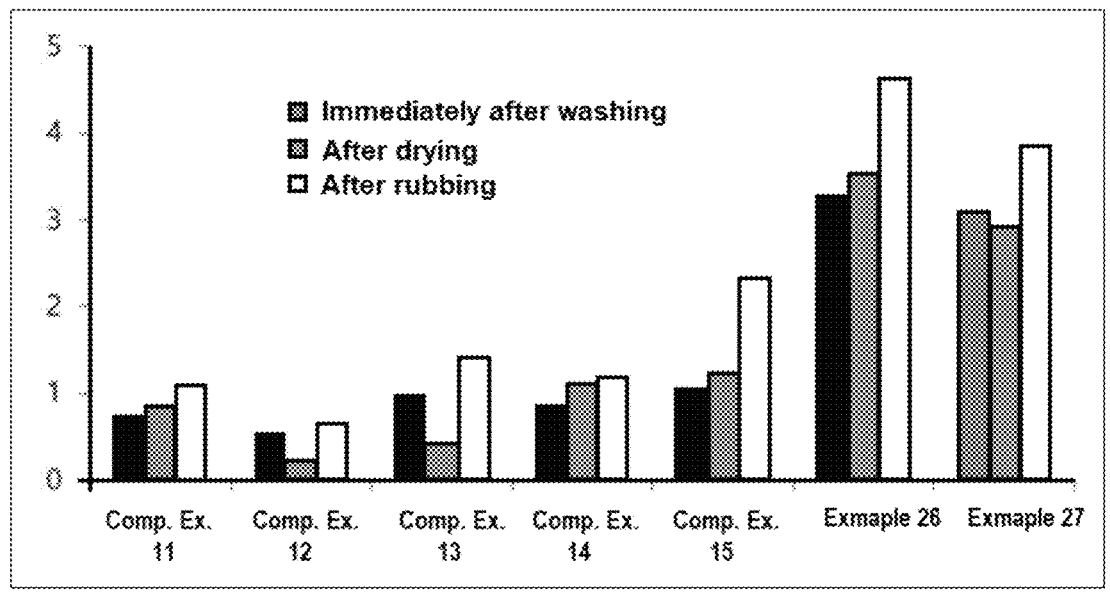
[FIG. 6]
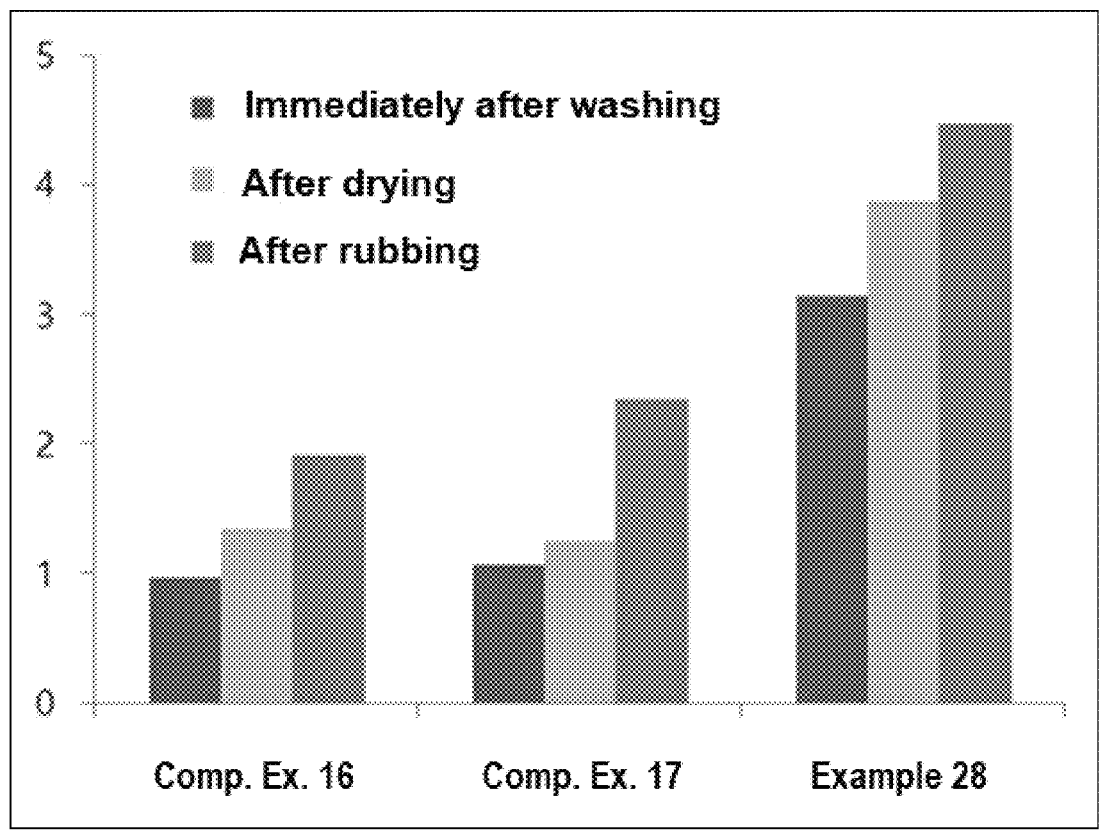

METHOD FOR PREPARING ORGANIC-INORGANIC HYBRID MICROCAPSULE

TECHNICAL FIELD

Cross-Reference to Related Application

This application claims the benefits of Korean Patent Applications No. 10-2018-0077239 filed on Jul. 3, 2018 and No. 10-2018-0077240 filed on Jul. 3, 2018 with the Korean Intellectual Property Office, the disclosure of which is incorporated herein by reference in its entirety.

The present disclosure relates to a method for preparing an organic-inorganic hybrid microcapsule. More specifically, it relates to a method for preparing an organic-inorganic hybrid microcapsule capable of stably supporting an active ingredient and then effectively expressing its activity by pressure, and exhibiting a characteristic of gradually releasing the active ingredient at room temperature unlike the prior art.

BACKGROUND OF ART

Encapsulation is known as a method for solving the problem that losing intrinsic properties of active ingredients due to factors such as light and heat during storage, or inferior activity caused by low concentration due to physical phenomena such as evaporation. The encapsulation has an advantage of not only enhancing stability of the active ingredient, but also enabling the active ingredient to be activated at a time desired by the user, and thus, is used in many industrial fields. As a representative method of activating the encapsulated active ingredient, there is a method of gradually releasing or sustaining the active ingredient by inducing the destruction of the outer wall of the capsule by pressure, etc., or inducing the formation of a small hole in the outer wall of the capsule.

A melamine-formaldehyde resin-based capsule is known as a commercially widely used encapsulation material, but there is a problem that formaldehyde, which is a toxic substance, must exist in the manufacturing process of the microcapsule. For this reason, interest in new capsules without formaldehyde is increasing.

As a solution to this, liposome capsules, coacervation, and microsponges have been proposed. However, these methods are insufficient to replace melamine capsules as they have limitations in that stability of the capsule is reduced, supporting capacity of the active ingredient is reduced, or release is not controlled by the surfactant and ionic components in the formulation.

In another way, capsules based on inorganic materials such as silica have been proposed as a new alternative. However, as amphiphilicity of the core material increases, the capsule prepared by the above method has difficulty in forming an outer wall after organopolysiloxane, which is a precursor, moves to the interface, and thus there is a problem in wide application. In addition, the capsule has a disadvantage in that it is difficult to control the degree of activation of the active ingredient due to its low elasticity and high hardness.

Meanwhile, there are capsules based on organic polymers such as polyacryl, polyurea, and polyurethane that are widely used industrially, and the capsules are considered as an alternative due to an advantage of not using formaldehyde in the polymerization process, versatility, and excellent economical efficiency. However, the organic polymer-based capsule has high elasticity of the polymer itself, so that it has difficulty in expressing activity of the active ingredient due to its poor fracturability by pressure.

Therefore, there is a need to develop a new capsule material that is economical and can easily control the activity of an active ingredient, while having few toxic substances with high versatility.

DETAILED DESCRIPTION OF THE INVENTION

Technical Problem

In the present disclosure, there is provided a method for preparing an organic-inorganic hybrid microcapsule capable of easily expressing an activity of active ingredients and having an excellent characteristic of gradually releasing the active ingredient at room temperature, while having few toxic substances with high versatility and good economical efficiency.

In the present disclosure, there is also provided a microcapsule including an organic-inorganic hybrid outer wall prepared by the above method.

Technical Solution

In the present disclosure, there is provided a method for preparing an organic-inorganic hybrid microcapsule including the steps of:

a first step of preparing a first continuous-phase solution containing inorganic nanoparticles and a second continuous-phase solution containing a polymer precursor 1 for reinforcing an outer wall;

a second step of preparing a dispersed-phase solution containing a polymer precursor 2 which reacts with the polymer precursor 1 or containing an active ingredient and the polymer precursor 2; and a third step of forming a pickering emulsion by adding the dispersed-phase solution to the first solution, and then forming an outer wall of the capsule through interfacial polymerization by adding the second solution, wherein the outer wall of the capsule includes i) at least one polymer selected from the group consisting of polyamide, polyurethane, polyurea, polyester and poly($\beta$-amino ester), and ii) inorganic nanoparticles; and the polymer precursor 1 for reinforcing the outer wall and the polymer precursor 2 each independently contain at least one precursor for forming a polymer selected from the group consisting of polyamide, polyurethane, polyurea, polyester, and poly($\beta$-amino ester).

According to another embodiment of the present disclosure, there is provided an organic-inorganic hybrid microcapsule, including a dispersed phase which is a core, and a hybrid capsule outer wall formed at an interface of the dispersed phase and surrounding outside of the dispersed phase;

wherein the hybrid capsule outer wall is an inorganic nanoparticles-polymer resin composite containing i) at least one polymer selected from the group consisting of polyamide, polyurethane, polyurea, polyester and poly($\beta$-amino ester), and ii) inorganic nanoparticles.

Advantageous Effects

The present disclosure can provide an organic-inorganic hybrid microcapsule including a polymer and inorganic nanoparticles capable of easily expressing an activity of active ingredients by controlling strength of an outer wall of the capsule, and having an excellent characteristic that an internal dispersed phase is gradually released over time, while having few toxic substances with high versatility and good economical efficiency.

In addition, the present disclosure can provide an organic-inorganic hybrid capsule having excellent biodegradability with the above characteristics.

The present disclosure can also provide an eco-friendly organic-inorganic hybrid capsule, when using a natural polymer, a derivative thereof, and a naturally-derived polymer as a precursor in the preparation of the capsule.

BRIEF DESCRIPTION OF THE DRAWINGS

FIG. 1 schematically shows a contact angle of inorganic nanoparticles.

FIG. 2 shows the principle of the method for preparing an organic-inorganic hybrid capsule of the present disclosure.

FIG. 3 shows a comparison of release behaviors of volatile oil over time in Comparative Examples 1, 6, Examples 1 and 14 to 17.

FIG. 4 shows a comparison of release behaviors of volatile oil over time in Comparative Examples 2, 6, Examples 6 and 18 to 21 in which a composition of the dispersed phase was changed.

FIG. 5 shows a comparison of laundry evaluation results in Comparative Examples 11 to 15 and Examples 26 to 27.

FIG. 6 shows a comparison of laundry evaluation results of Comparative Examples 16 to 17 and Example 28 in which a composition of the dispersed phase was changed.

DETAILED DESCRIPTION OF THE EMBODIMENTS

As the present invention can be variously modified and have various forms, specific embodiments thereof are shown by way of examples and will be described in detail. However, it is not intended to limit the present invention to the particular form disclosed and it should be understood that the present invention includes all modifications, equivalents, and replacements within the idea and technical scope of the present invention.

The terms "include", "comprise", and the like of the present disclosure are used to specify certain features, regions, integers, steps, operations, elements, and/or components, and these do not exclude the existence or the addition of other certain features, regions, integers, steps, operations, elements, and/or components.

In general, a diameter of the microcapsule may be 1 to 1,000 µm. In the context of the present disclosure, the term "microcapsule" also includes nanocapsules, which have a diameter of <1 µm. However, the diameter of the capsule is preferably in the range of 1 to 100 µm, preferably 2 to 50 µm. A thickness of the wall can be, for example, 0.05 to 10 µm.

Hereinafter, the method for preparing an organic-inorganic hybrid microcapsule according to a specific embodiment of the present disclosure and the microcapsule prepared using the same will be described.

In order to solve the conventional problem, the present disclosure provides a method for preparing an organic-inorganic hybrid microcapsule including a first step of adding inorganic nanoparticles and an outer wall reinforcing material capable of forming a polymer such as polyamide and polyurethane to a continuous phase, a second step of adding a reactive material capable of forming a polymer such as polyamide by reacting with the outer wall reinforcing material to a dispersed phase with or without an active ingredient, and a third step of polymerizing the outer wall of the capsule after forming a pickering emulsion by mixing the continuous phase and the dispersed phase.

Preferably, the outer wall of the capsule may include an organic-inorganic hybrid structure containing at least one polymer selected from the group consisting of polyamide, polyurethane, polyurea, and polyester and inorganic nanoparticles.

Specifically, according to an embodiment of the present disclosure, there is provided a method for preparing an organic-inorganic hybrid microcapsule including the steps of:

a first step of preparing a first continuous-phase solution containing inorganic nanoparticles and a second continuous-phase solution containing a polymer precursor 1 for reinforcing an outer wall;

a second step of preparing a dispersed-phase solution containing a polymer precursor 2 which reacts with the polymer precursor 1 or containing an active ingredient and the polymer precursor 2; and a third step of forming a pickering emulsion by adding the dispersed-phase solution to the first solution, and then forming an outer wall of the capsule through interfacial polymerization by adding the second solution, wherein the outer wall of the capsule includes i) at least one polymer selected from the group consisting of polyamide, polyurethane, polyurea, polyester and poly(β-amino ester), and ii) inorganic nanoparticles; and the polymer precursor 1 for reinforcing the outer wall and the polymer precursor 2 each independently contain at least one precursor for forming a polymer selected from the group consisting of polyamide, polyurethane, polyurea, polyester, and poly(β-amino ester).

The present disclosure is characterized in that the organic-inorganic hybrid microcapsule having few toxic substances with high versatility and economical efficiency is provided by allowing polymerization of an outer wall reinforcing material and a reactive material to proceed at the interface after preparing a continuous phase containing the outer wall reinforcing material and inorganic nanoparticles, and then preparing a pickering emulsion by mixing the continuous phase with a dispersed phase containing the reactive material with or without an active ingredient, so that the polymer and inorganic nanoparticles can be included at the interface in the preparation of the capsule.

In addition, since inorganic nanoparticles are included in the outer wall of the capsule, hardness and elasticity of the outer wall can be adjusted, and a capsule capable of easily expressing the activity of the active ingredient can be prepared.

Additionally, the present disclosure can prepare an eco-friendly organic-inorganic hybrid capsule when using a natural polymer, a derivative thereof, and a naturally-derived polymer as a precursor.

Herein, the method for preparing a microcapsule of the present disclosure can be carried out in three steps.

The first step is to first prepare a continuous phase in order to form a pickering emulsion to be described later.

The continuous phase may contain a reactive material which is a precursor of an outer wall material of the capsule to be generated in the encapsulation process. The continuous phase refers to a material maintaining in a liquid state at room temperature, and may mean a solution containing at least one solvent generally used in the process.

In addition, the continuous phase may include a first continuous-phase solution containing inorganic nanoparticles dispersed therein and a second continuous-phase solution containing a polymer material.

Preferably, the first continuous-phase solution may contain inorganic nanoparticles as a precursor of the outer wall material of the capsule, and the second continuous-phase solution may contain a polymer precursor for reinforcing the outer wall.

The inorganic nanoparticles function as pickering particles that increase stability of the dispersed phase in the interfacial polymerization process, and are mixed in the polymer polymerization process to increase hardness and lower elasticity of the capsule outer wall.

The inorganic nanoparticles may be contained in an amount of 0.001 to 30 wt % based on a total weight of the first continuous-phase solution. The inorganic nanoparticles may be contained in an amount of 0.001 parts by weight to 100 parts by weight, preferably 0.005 parts by weight to 75 parts by weight, and more preferably 0.01 parts by weight to 50 parts by weight, based on 100 parts by weight of a total weight of the dispersed solution. When 0.001 parts by weight or less (0.001 wt % or less based on the first solution) of the inorganic nanoparticles are contained, there is a problem that the pickering emulsion cannot be formed. When 100 parts by weight or more (30 wt % or more based on the first solution) of the inorganic nanoparticles are contained, there is a problem that a gel is formed, resulting in high viscosity.

The inorganic nanoparticles may have a diameter of 1 nm or more and 900 nm or less, preferably 1.5 nm or more and 750 nm or less, and more preferably 2 nm or more and 500 nm or less.

The inorganic nanoparticles may be at least one selected from the group consisting of halloysite nanotubes, laponite, kaolinite clay, colloidal silica, calcium hydroxide, magnesium hydroxide, magnesium oxide, alumina, aluminum hydroxide, aluminum phosphate, calcium pyrrolate, aluminum pyrrolate, and zinc pyrrolate.

Meanwhile, the first step may further include a step of performing surface treatment of the inorganic nanoparticles.

A contact angle 8 used to define properties of the inorganic nanoparticles may be defined as shown in FIG. 1. As shown in FIG. 1, a tangent line is drawn at the point where the inorganic nanoparticles, which are located at the horizontal interface of the continuous phase and the dispersed phase, meet the interface, and an angle formed by the tangent line and the interface in the continuous phase is called the contact angle.

The inorganic nanoparticles are materials having a contact angle of 90 degrees or less, when exist in the continuous phase and the dispersed phase. Such inorganic nanoparticles may be controlled to function as pickering particles by the surface treatment.

Accordingly, the first step may further include a surface treatment step of making the inorganic nanoparticles have a contact angle of 90° or less between the continuous phase and the dispersed phase. Through the surface treatment, the contact angle of the inorganic nanoparticles may be 0° or more and 90° or less, preferably 5° or more and 90° or less, and more preferably 10° or more and 90° or less.

The surface treatment step may be performed including a step of adding a surface treatment material for adjusting the contact angle of the inorganic nanoparticles to the first continuous-phase solution containing the inorganic nanoparticles.

The surface treatment material may include a non-covalent surface treatment material such as cetyltrimethylammonium bromide, cetyltrimethylammonium chloride, distearyldimonium chloride, and aluminium stearate, a halosilane-based material or a covalent surface treatment material such as alkoxysilane and a derivative thereof, and at least one selected from the above materials may be used.

In addition, the first continuous-phase solution may contain distilled water as a residual amount of solvent in addition to the inorganic nanoparticles. The distilled water may be purified and used according to a method well known in the art.

Meanwhile, the second continuous-phase solution contains a polymer precursor 1 for reinforcing an outer wall. The polymer precursor 1 refers to a material for reinforcing the outer wall included in the continuous phase, which is soluble in the continuous phase and forms the outer wall of the capsule by reacting with a reactive material later.

The polymer precursor 1 may be contained in an amount of 0.001 to 20 wt % based on a total weight of the second continuous-phase solution. The polymer precursor 1 for reinforcing the outer wall may be contained in an amount of 0.002 to 30 parts by weight, preferably 0.006 to 25 parts by weight, more preferably 0.011 to 20 parts by weight, based on 100 parts by weight of a total weight of the dispersed solution. When 0.002 parts by weight or less (0.001 wt % or less based on the second solution) of the polymer precursor 1 is contained, there is a problem that the capsule is not formed. When 30 parts by weight or more (20 wt % or more based on the second solution) of the polymer precursor 1 is contained, there is a problem that stability of the capsule is deteriorated due to a non-uniform reaction.

The polymer precursor 1 for reinforcing the outer wall contains at least one precursor for forming a polymer selected from the group consisting of polyamide, polyurethane, polyurea, polyester, and poly(β-amino ester).

As a representative example, the polymer precursor 1 may be at least one selected from the group consisting of a compound having two or more amine groups, a compound having two or more hydroxyl groups, and a natural polymer.

For example, the compound having two or more amine groups may include a compound represented by the following Chemical Formula 1.

[Chemical Formula 1]

$$H_2N{-}\!\!\left[R_1\right]_{\!n}\!\!{-}NH_2$$

(in Chemical Formula 1, each $R_1$ may independently include C1 to C50 alkylene, a C3 to C60 cyclic hydrocarbon group, or C1 to C50 alkylene and a C3 to C60 cyclic hydrocarbon group having or not having at least one amine group or at least one heteroatom, and n is an integer of 1 to 5000)

In the present disclosure, the C3 to C30 cyclic hydrocarbon may each independently include a cyclic saturated or unsaturated hydrocarbon (aromatic hydrocarbon) having or not having at least one amine group or at least one heteroatom.

More specifically, the compound having two or more amine groups may be at least one selected from the group consisting of methylenediamine, ethylenediamine, diethylenetriamine, triethylenetetramine, tetraethylenepentamine, tris(2-aminoethyl)amine, polyethyleneimine, poly(propylene glycol) bis(2-aminopropyl ether), trimethylolpropane tris[poly(propylene glycol), amine terminated]ether, poly (ethylene glycol) bis(amine), o-phenylenediamine, p-phenylenediamine, m-phenylenediamine, 2,4-diaminotoluene, 2,3-diaminotoluene, 2,5-diaminotoluene, 3,3'-diaminodiphenylmethane, 3,4'-diaminodiphenylmethane, 4,4'-diaminodiphenylmethane, 4,4'-ethylenedianiline, 4,4'-diaminodiphenyl sulfide, 4,4'-oxydianiline, pararosaniline base, melamine and tetrakis(4-aminophenyl)methane).

The compound having two or more hydroxyl groups may include a compound represented by the following Chemical Formula 2.

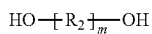
[Chemical Formula 2]

(in Chemical Formula 2, each $R_2$ may independently include C1 to C50 alkylene, a C3 to C60 cyclic hydrocarbon group, or C1 to C50 alkylene and a C3 to C60 cyclic hydrocarbon group having or not having at least one hydroxyl group or at least one heteroatom, and m is an integer of 1 to 5000)

More specifically, the compound having two or more hydroxyl groups may be at least one selected from the group consisting of methanediol, ethyelene glycol, propanediol, butanediol, pentanediol, hexanediol, heptanediol, octanediol, nonanediol, decanediol, dodecanediol, tetradecanediol, hexadecanediol, threitol, ribitol, galactitol, fucitol, iditol, inositol, volemitol, maltotriitol, maltotetraitol, polyglycitol, arabitol, erythritol, glycerol, Isomalt, lactitol, maltitol, mannitol, sorbitol, xylitol, sucrose, polyethylene glycol, polypropylene glycol, polyvinyl alcohol, VP/vinyl alcohol copolymer), butendiol/vinyl alcohol copolymer, polyglycerin, glyceryl polyacrylate, dimethiconol, bis-hydroxyethoxypropyl dimethicone, bis-hydroxypropyl dimethicone, hydroxypropyldimethicone and bis-hydroxyethyl tromethamine.

In addition, at least one selected from the group consisting of a natural polymer, a derivative thereof, and a naturally-derived polymer may be used as a polymer precursor capable of interfacial polymerization in order to prepare eco-friendly capsules. Examples of the natural polymer include a material containing two or more amine groups such as gelatin, chitosan, and polylysine, and a material containing two or more hydroxyl groups such as gum arabic, polysaccharides, pectin, and alginate.

In addition, the second continuous-phase solution may contain distilled water as a residual amount of solvent in addition to the polymer precursor 1. The distilled water may be purified and used according to a method well known in the art.

Meanwhile, the second step is to prepare a dispersed phase for mixing with the continuous phase.

The dispersed phase contains a specific reactive material, or a reactive material and an active ingredient, wherein the reactive material is a precursor of a material for the outer wall of the capsule to be generated in the encapsulation process. The dispersed phase refers to a material maintaining in a liquid state at room temperature, and refers to one or more solvents generally used in the process. When an active ingredient is a liquid at room temperature, the active ingredient may be used as the dispersed phase.

In addition, the dispersed phase refers to a solvent which is not mixed with the continuous phase. When the continuous phase is water, examples of the dispersed phase include a linear or nonlinear hydrocarbon-based solvent such as pentane, hexane, cyclohexane, heptane, octane, isododecane and dodecane, an ether group-containing derivative-based solvent such as ethyl ether, butyl ether and methyl-t-butyl ether, an ester group-containing derivative-based solvent such as ethyl acetate, butyl acetate and ethyl butyrate, a ketone-based solvent such as methyl ethyl ketone, an aromatic solvent such as benzene, toluene and xylene, a haloalkane-based solvent such as dichloromethane, dichloroethane, chloroform and carbon tetrachloride, and a silicone-based solvent such as dimethicone and cyclomethicone. At least one of these may be selected and used.

In addition, the above-mentioned solvent applicable to the dispersed phase may be applied as a continuous phase, if necessary.

In the dispersed phase solution, the solvent may be included in a residual amount, and may be appropriately adjusted according to the added components.

The dispersed phase contains a reactive material which is a precursor of a material for the outer wall of the capsule. The reactive material is a material that can form the outer wall of the capsule by reacting with an outer wall reinforcing material dissolved in the continuous phase, and is well soluble in the dispersed phase.

This reactive material is referred to as a polymer precursor 2 in the present disclosure. The polymer precursor 2 includes a precursor that interfacially reacts with the polymer precursor 1 for reinforcing the outer wall to form a polymer such as polyamide on the outer wall of the capsule.

According to a preferred embodiment, at least one selected from the group consisting of a compound containing two or more acid chloride structures represented by the Chemical Formula 3, a compound containing two or more isocyanate structures represented by the following Chemical Formula 4, and a compound containing two or more chloroformate structures represented by the following Chemical Formula 5 may be used.

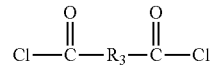
[Chemical Formula 3]

(in Chemical Formula 3, each $R_3$ may independently include C1 to C50 alkylene, a C3 to C60 cyclic hydrocarbon group, or C1 to C50 alkylene and a C3 to C60 cyclic hydrocarbon group having or not having at least one acid chloride (—COCl) or at least one heteroatom)

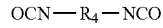
[Chemical Formula 4]

(in Chemical Formula 4, each $R_4$ may independently include C1 to C50 alkylene, a C3 to C60 cyclic hydrocarbon group, or C1 to C50 alkylene and a C3 to C60 cyclic hydrocarbon group having or not having at least one isocyanate or at least one heteroatom)

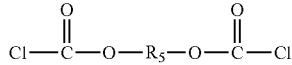
[Chemical Formula 5]

(in Chemical Formula 5, each $R_5$ may independently include C1 to C50 alkylene, a C3 to C60 cyclic hydrocarbon group, or C1 to C50 alkylene and a C3 to C60 cyclic hydrocarbon group having or not having at least one chloroformate (—OCOCl) or at least one heteroatom)

The polymer precursor 2 may be a compound containing two or more acrylate structures represented by the following Chemical Formula 6.

[Chemical Formula 6]

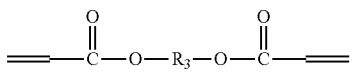

(in Chemical Formula 6, each $R_3$ may independently include C1 to C50 alkylene, a C3 to C60 cyclic hydrocarbon group, or C1 to C50 alkylene and a C3 to C60 cyclic hydrocarbon group having or not having at least one acrylate or at least one heteroatom)

More specifically, the compound containing two or more acid chlorides may be at least one selected from the group consisting of malonyl chloride, succinyl chloride, glutaryl chloride, adipoyl chloride, pimeloyl chloride, suberoyl chloride, sebacoyl chloride, azelaic acid dichloride and dodecanedioyl dichloride.

More specifically, the compound containing two or more isocyanates may be at least one selected from the group consisting of methylene diisocyanate, 1,4-phenylene diisocyanate, tolylene-2,4-diisocyanate, 1-chloromethyl-2,4-diisocyanatobenzene, 4-chloro-6-methyl-1,3-phenylene diisocyanate, 1,3-bis(1-isocyanato-1-methylethyl)benzene, 3,3'-dimethyl-4,4'-biphenylene diisocyanate, 3,3'-dichloro-4,4'-diisocyanato-1,1'-biphenyl, 4,4'-oxybis(phenyl isocyanate), 4,4'-methylenebis(phenyl isocyanate), 4,4'-methylenebis(2,6-diethylphenyl isocyanate), isophorone diisocyanate, trans-1,4-cyclohexylene diisocyanate, 1,3-bis(isocyanatomethyl) cyclohexane, 4,4'-methylenebis(cyclohexyl isocyanate), diisocyanatobutane, hexamethylene diisocyanate, diisocyanatooctane, diisocyanatododecane and 1,6-diisocyanato-2,2,4-trimethylhexane.

More specifically, the compound containing two or more chloroformates may be at least one selected from the group consisting of ethylenebis(chloroformate), diglycolyl chloride, oxydiethylene bis(chloroformate), tri(ethylene glycol) bis(chloroformate), 1,4-phenylene bis(chloroformate), bisphenol A bis(chloroformate) and bisphenol Z bis(chloroformate).

More specifically, the compound containing two or more acrylate groups may be at least one selected from the group consisting of ethylene glycol diacrylate, di(ethylene glycol) diacrylate, tri(ethylene glycol) diacrylate, tetra(ethylene glycol) diacrylate, poly(ethylene glycol) diacrylate, propylene glycol diacrylate, di(propylene glycol) diacrylate, tri(propylene glycol) diacrylate, tetra(propylene glycol) diacrylate, poly(propylene glycol) diacrylate, butanediol diacrylate, hexanediol diacrylate, hexanediol ethoxylate diacrylate, neopentyl glycol propoxylate (1 PO/OH) diacrylate, trimethylolpropane ethoxylate (1 EO/OH) methyl ether diacrylate, neopentyl glycol diacrylate, pentaerythritol triacrylate, trimethylolpropane triacrylate, trimethylolpropane propoxylate triacrylate, tris[2-(acryloyloxy)ethyl] isocyanurate, trimethylolpropane ethoxylate triacrylate, di(trimethylolpropane) tetraacrylate, pentaerythritol tetraacrylate, and hydroxypivalyl hydroxypivalate bis[6-(acryloyloxy)hexanoate.

The polymer precursor 2 may be contained in an amount of 0.001 to 30 wt %, preferably 0.005 to 25 wt %, more preferably 0.01 to 20 wt %, based on a total weight of the dispersed solution. When 0.001 wt % or less of the polymer precursor 2 is contained, there is a problem that the capsule is not formed. When 30 wt % or more of the polymer precursor 2 is contained, there is a problem that stability of the capsule is deteriorated due to a non-uniform reaction.

The active ingredient is a substance that is desired to maintain its activity by the capsule to be prepared, and is a substance whose activity is expressed by destruction of the outer wall later. When the active ingredient is a liquid at room temperature, it may replace the dispersed phase, which is a solvent. Otherwise, it may vary depending on solubility. Examples of the active ingredient may include fragrance, dye, catalyst, antioxidant, drug, and the like, and at least one of these may be selected and used.

Even if the active ingredient is contained in a small amount, its properties can be expressed. In addition, since the active ingredient itself may be a dispersed phase, it may be included up to 100 parts by weight based on 100 parts by weight of the dispersed-phase solution, if necessary. Accordingly, the content of the active ingredient is not particularly limited and may be set according to the ingredients used, and the active ingredient may be used according to a method known in the art.

Meanwhile, the third step is to form an organic-inorganic hybrid microcapsule by forming a pickering emulsion using a continuous-phase solution and a dispersed-phase solution, and then performing interfacial polymerization.

Specifically, as shown in FIG. 2, the microcapsule of the present disclosure is formed by interfacial polymerization after mixing the continuous-phase solution and the dispersed-phase solution to form a pickering emulsion. The polymer and inorganic nanoparticles, which are materials of the outer wall of the capsule, are present at the interface.

More specifically, the first continuous-phase solution and the dispersed-phase solution are mixed to form a pickering emulsion, and then the second continuous-phase solution is added thereto, followed by interfacial polymerization to form the microcapsule.

In the third step, when the pickering emulsion is formed by mixing the first continuous-phase solution and the dispersed-phase solution, stirring conditions may be 10 RPM or more and 16000 RPM or less, preferably 50 RPM or more and 13000 RPM or less, and more preferably 100 RPM or more and 10000 RPM or less.

In addition, the interfacial polymerization after the addition of the second continuous-phase solution may be performed at 0 to 100° C. for 1 to 48 hours, preferably at 10 to 90° C. for 2 to 24 hours, and more preferably at 20 to 80° C. for 3 to 12 hours. Herein, stirring conditions may be 10 RPM or more and 6000 RPM or less, preferably 50 RPM or more and 5000 RPM or less, and more preferably 100 RPM or more and 4000 RPM or less.

If necessary, the method of the present disclosure may further include a step of adding a dispersion stabilizer in the preparation of the capsule. Specifically, the dispersion stabilizer may be used when forming the outer wall of the capsule.

According to a preferred embodiment, the method of the present disclosure may further include the step of adding a dispersion stabilizer in the first step or in the third step.

The dispersion stabilizer may be used for the purpose of enhancing dispersibility of the capsule to be prepared after the reaction. As the dispersion stabilizer, at least one selected from the group consisting of gum arabic, polysaccharides, pectin, alginate, arabinogalactan, carrageenan, gellan gum, xanthan gum, guar gum, acrylate/acrylic polymer, starch, water-swellable clay, acrylate/aminoacrylate copolymer, and a mixture thereof, maltodextrin; natural gum such as alginate ester; gelatin, protein hydrolysate, and a quaternized form thereof; and synthetic polymers and copolymers such as poly(vinyl pyrrolidone-co-vinyl acetate), poly(vinyl alcohol-co-vinyl acetate), poly(maleic acid), poly(alkylene oxide), poly(vinylmethyl ether), poly(vinyl ether-co-maleic anhydride), poly(ethyleneimine), poly((meth)acrylamide), poly(alkyleneoxide-co-dimethylsiloxane), or poly(aminodimethylsiloxane) may be used.

The dispersion stabilizer may be used in an amount within a range well known in the art.

After the polymerization in the third step, a step of concentrating or/and drying the solution containing the microcapsule may be further included, if necessary, and the conditions are not particularly limited.

In addition, the pH can be adjusted using an acidic substance or a basic substance, and the conditions are not particularly limited.

According to another embodiment of the present disclosure, there is provided an organic-inorganic hybrid microcapsule prepared by the above-described method including a dispersed phase located in a core and a hybrid capsule outer wall surrounding the outside of the dispersed phase, wherein the dispersed phase is contained in an amount of 1 to 90 wt % based on a total weight of the capsule.

More specifically, there is provided an organic-inorganic hybrid microcapsule, including a dispersed phase which is a core, and a hybrid capsule outer wall formed at an interface of the dispersed phase and surrounding outside of the dispersed phase;

wherein the hybrid capsule outer wall is an inorganic nanoparticles-polymer resin composite containing i) at least one polymer selected from the group consisting of polyamide, polyurethane, polyurea, polyester and poly(β-amino ester), and ii) inorganic nanoparticles.

In the organic-inorganic hybrid microcapsule of the present disclosure, as shown in FIG. 2, the dispersed phase is located in the core, and the organic-inorganic hybrid outer wall formed by interfacial polymerization is formed outside the dispersed phase.

Preferably, the microcapsule may include a dispersed phase; and a hybrid capsule outer wall formed at an interface of the dispersed phase and containing at least one polymer selected from the group consisting of polyamide, polyurethane, polyurea, polyester and poly(β-amino ester), and inorganic nanoparticles.

In addition, the dispersed phase may contain at least one selected from the group consisting of a compound containing two or more acid chloride structures represented by the Chemical Formula 3, a compound containing two or more isocyanate structures represented by the following Chemical Formula 4, and a compound containing two or more chloroformate structures represented by the following Chemical Formula 5; or a compound containing two or more acrylate structures represented by the following Chemical Formula 6.

[Chemical Formula 3]

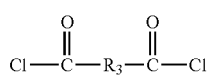

(in Chemical Formula 3, each $R_3$ may independently include C1 to C50 alkylene, a C3 to C60 cyclic hydrocarbon group, or C1 to C50 alkylene and a C3 to C60 cyclic hydrocarbon group having or not having at least one acid chloride (—COCl) or at least one heteroatom)

[Chemical Formula 4]

OCN—$R_4$—NCO (in Chemical Formula 4, each $R_4$ may independently include C1 to C50 alkylene, a C3 to C60 cyclic hydrocarbon group, or C1 to C50 alkylene and a C3 to C60 cyclic hydrocarbon group having or not having at least one isocyanate or at least one heteroatom)

[Chemical Formula 5]

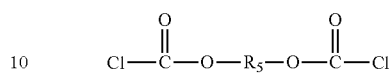

(in Chemical Formula 5, each $R_5$ may independently include C1 to C50 alkylene, a C3 to C60 cyclic hydrocarbon group, or C1 to C50 alkylene and a C3 to C60 cyclic hydrocarbon group having or not having at least one chloroformate (—OCOCl) or at least one heteroatom)

[Chemical Formula 6]

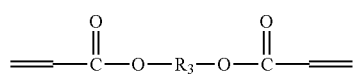

(in Chemical Formula 6, each $R_3$ may independently include C1 to C50 alkylene, a C3 to C60 cyclic hydrocarbon group, or C1 to C50 alkylene and a C3 to C60 cyclic hydrocarbon group having or not having at least one acrylate or at least one heteroatom)

Herein, the polymer resin contained in the inorganic nanoparticles-polymer resin composite is formed by a reaction between the outer wall reinforcing material and the reactive material as described above, and may be formed using a catalyst. In this case, the catalyst may be included on the outer wall of the final capsule structure.

In addition, since the inorganic nanoparticles are included in the interfacial polymerization process, hardness and elasticity of the outer wall of the capsule are adjusted to improve fracturability.

In addition, the dispersed phase may be contained in the organic-inorganic hybrid microcapsule in an amount of 1 to 90 wt %, preferably 3 to 85 wt %, more preferably 5 to 80 wt % based on a total weight of the microcapsule.

The outer wall of the organic-inorganic hybrid capsule included after being polymerized at the interface of the microcapsule can be adjusted in strength compared to the conventional one, so that the activity of active ingredients can be easily expressed. In particular, the organic-inorganic hybrid capsule of the present disclosure may have strength suitable for product application, for example, the strength of about 40 to 200 MPa, about 45 to 170 MPa, or about 50 to 160 MPa, and the strength may be easily adjusted within the above range when applied to products. Herein, the strength of capsules may be measured using a nanoindentation test device (CMS instrument), and then obtained by dividing the maximum load value by the contact area.

In addition, an average particle diameter of the microcapsule of the present disclosure may be 0.1 μm or more and 1000 μm or less.

Hereinafter, the function and effect of the present invention will be described in more detail through specific examples. However, these examples are for illustrative purposes only, and the invention is not intended to be limited by these examples.

EXAMPLES

In the present disclosure, the strength and size of capsules were evaluated in the following manner.

(1) Strength

The strength of capsules was measured using a nanoindentation test device (CMS instrument). Herein, the strength of capsules was obtained by dividing the maximum load value by the contact area.

(2) Size

The size of capsules was measured using Mastersizer 3000 manufactured by Malvern.

[Experimental Example 1] Strength Comparison of Capsules to which Various Inorganic Nanoparticles are Applied In order to apply microcapsules to products, an appropriate strength is required. If the strength of microcapsules is too high, it is difficult to apply them to products, so it is important to control the strength. Accordingly, strength comparison was conducted for the conventional organic microcapsules and the organic-inorganic hybrid microcapsules according to the method of the present disclosure.

Specifically, organic microcapsules of Comparative Examples and organic-inorganic hybrid capsules based on inorganic nanoparticles of Examples were prepared in the following manner, and the strength and size of each capsule were measured. In addition, the results of Comparative Example 1 and Examples 1 to 5 and the results of Comparative Example 2 and Examples 6 to 10 in which the composition of the dispersed-phase solution was changed were compared, and are shown in Tables 1 and 2.

Comparative Example 1

The First Step 0.15 g of sodium dodecyl sulfate was dispersed in 59.85 g of distilled water to prepare a continuous phase 1 (first solution). In addition, 1 g of polyethyleneimine was added to 9 g of distilled water and mixed to prepare a continuous phase 2 (second solution).

The Second Step 0.5 g of polyisocyanate was added to 29.5 g of dodecane and mixed to prepare a dispersed-phase solution.

The Third Step

Under the conditions of 2000 RPM, the dispersed-phase solution was slowly added to the continuous phase 1 (first solution) and stirred to prepare an emulsion. Thereafter, the speed of the stirrer was lowered to 1000 RPM, and the continuous phase 2 (second solution) was added to the emulsion, followed by interfacial polymerization at 80° C. for 12 hours to prepare a polyurea microcapsule.

Examples 1 to 5

The First Step

One of the inorganic nanoparticles (Silica, Laponite, Iron oxide, Alumina, Titanium oxide) were dispersed in 59 g of distilled water to prepare a continuous phase 1 (first solution). In addition, 1 g of polyethyleneimine was added to 9 g of distilled water to prepare a continuous phase 2 (second solution).

The Second Step 0.5 g of polyisocyanate was added to 29.5 g of dodecane to prepare a dispersed-phase solution.

The Third Step

Under the conditions of 2000 RPM, the dispersed-phase solution was slowly added to the continuous phase 1 (first solution) and stirred to prepare a pickering emulsion. Thereafter, the speed of the stirrer was lowered to 1000 RPM, and the continuous phase 2 (second solution) was added to the pickering emulsion, followed by interfacial polymerization at 80° C. for 12 hours to prepare an organic-inorganic hybrid microcapsule.

TABLE 1

|  | Comp. Ex. 1 | Ex. 1 | Ex. 2 | Ex. 3 | Ex. 4 | Ex. 5 |
| --- | --- | --- | --- | --- | --- | --- |
| Distilled Water | 68.85 | 68 | 68 | 68 | 68 | 68 |
| Silica | — | 1 | — | — | — | — |
| Laponite | — | — | 1 | — | — | — |
| Iron oxide | — | — | — | 1 | — | — |
| Alumina | — | — | — | — | 1 | — |
| Titanium oxide | — | — | — | — | — | 1 |
| Sodium dodecyl Sulfate | 0.15 | — | — | — | — | — |
| Polyisocyanate | 0.5 | 0.5 | 0.5 | 0.5 | 0.5 | 0.5 |
| Polyethyleneimine | 1 | 1 | 1 | 1 | 1 | 1 |
| Dodecane | 29.5 | 29.5 | 29.5 | 29.5 | 29.5 | 29.5 |
| Strength (MPa) | 514.1 | 69.5 | 78.3 | 56.3 | 80.9 | 65.4 |
| Size (μm) | 25.3 | 18.2 | 16.4 | 22.7 | 16.8 | 19.7 |

As shown in Table 1, the organic microcapsule of Comparative Example 1 had too high strength, such as 514.1 MPa, so that it was difficult to apply it to a product and strength control was also difficult.

On the other hand, the organic-inorganic hybrid microcapsules of Examples 1 to 5 of the present disclosure were similar in size, and had strength suitable for use in products of about 56.3 to 80.9 MPa. In addition, Examples 1 to 5 showed an advantage of easy strength control, thereby improving processability and usability.

Comparative Example 2

The First Step 0.15 g of sodium dodecyl sulfate was dispersed in 59.85 g of distilled water to prepare a continuous phase 1 (first solution). In addition, 1 g of polyethyleneimine was added to 9 g of distilled water and mixed to prepare a continuous phase 2 (second solution).

The Second Step 0.5 g of 1,6-hexanediol diacrylate was added to 29.5 g of dodecane and mixed to prepare a dispersed-phase solution.

The Third Step

Under the conditions of 2000 RPM, the dispersed-phase solution was slowly added to the continuous phase 1 (first solution) and stirred to prepare an emulsion. Thereafter, the speed of the stirrer was lowered to 1000 RPM, and the continuous phase 2 (second solution) was added to the emulsion, followed by interfacial polymerization at 80° C. for 12 hours to prepare a poly(β-amino ester) microcapsule.

Examples 6 to 10

The First Step

One of the inorganic particles (Silica, Laponite, Iron oxide, Alumina, Titanium oxide) were dispersed in 59 g of distilled water to prepare a continuous phase 1 (first solution). In addition, 1 g of polyethyleneimine was added to 9 g of distilled water to prepare a continuous phase 2 (second solution).

The Second Step 0.5 g of 1,6-hexanediol diacrylate was added to 29.5 g of dodecane to prepare a dispersed-phase solution.

The Third Step

Under the conditions of 2000 RPM, the dispersed-phase solution was slowly added to the continuous phase 1 (first solution) and stirred to prepare a pickering emulsion. Thereafter, the speed of the stirrer was lowered to 1000 RPM, and the continuous phase 2 (second solution) was added to the pickering emulsion, followed by interfacial polymerization at 80° C. for 12 hours to prepare a biodegradable organic-inorganic hybrid microcapsule.

TABLE 2

|  | Comp. Ex. 2 | Ex. 6 | Ex. 7 | Ex. 8 | Ex. 9 | Ex. 10 |
|---|---|---|---|---|---|---|
| Distilled Water | 68.85 | 68 | 68 | 68 | 68 | 68 |
| Silica | — | 1 | — | — | — | — |
| Laponite | — | — | 1 | — | — | — |
| Iron oxide | — | — | — | 1 | — | — |
| Alumina | — | — | — | — | 1 | — |
| Titanium oxide | — | — | — | — | — | 1 |
| Sodium dodecyl Sulfate | 0.15 | — | — | — | — | — |
| 1,6-Hexanediol diacrylate | 0.5 | 0.5 | 0.5 | 0.5 | 0.5 | 0.5 |
| Polyethyleneimine | 1 | 1 | 1 | 1 | 1 | 1 |
| Dodecane | 29.5 | 29.5 | 29.5 | 29.5 | 29.5 | 29.5 |
| Strength (MPa) | 443.1 | 65.7 | 78.3 | 56.3 | 80.9 | 65.4 |
| Size (μm) | 27.1 | 17.5 | 15.9 | 23.4 | 19.6 | 18.2 |

As shown in Table 2, the organic microcapsule of Comparative Example 2 had too high strength, such as 443.1 MPa, so that it was difficult to apply it to a product and strength control was also difficult.

On the other hand, the organic-inorganic hybrid microcapsules of Examples 6 to 10 of the present disclosure were similar in size, and had strength suitable for use in products of about 56.3 to 80.9 MPa. In addition, Examples 1 to 5 showed an advantage of easy strength control, thereby improving processability and usability.

[Experimental Example 2] Strength Comparison of Capsules to which Various Polymer Materials are Applied Organic-inorganic hybrid capsules based on various polymer materials of Comparative Examples 3 to 5 and Examples 11 to 13 were prepared in the following manner, and the strength and size of each capsule were measured. The results are shown in Table 3.

Comparative Example 3

The First Step 0.15 g of sodium dodecyl sulfate was dispersed in 59.85 g of distilled water to prepare a continuous phase 1 (first solution). In addition, 1 g of polyethyleneimine was added to 9 g of distilled water and mixed to prepare a continuous phase 2 (second solution).

The Second Step 0.5 g of sebacoyl chloride was added to 29.5 g of dodecane to prepare a dispersed-phase solution.

The Third Step

Under the conditions of 2000 RPM, the dispersed phase was slowly added to the continuous phase 1 and stirred to prepare an emulsion. Thereafter, the speed of the stirrer was lowered to 1000 RPM, and the continuous phase 1 (first solution) was added to the emulsion, followed by interfacial polymerization at 80° C. for 12 hours to prepare a polyamide microcapsule.

Comparative Example 4

The First Step 0.15 g of sodium dodecyl sulfate was dispersed in 59.85 g of distilled water to prepare a continuous phase 1. In addition, 1 g of polyvinyl alcohol was added to 9 g of distilled water and mixed to prepare a continuous phase 2.

The Second Step 0.5 g of polyisocyanate was added to 29.5 g of dodecane and mixed to prepare a dispersed phase.

The Third Step

Under the conditions of 2000 RPM, the dispersed phase was slowly added to the continuous phase 1 and stirred to prepare an emulsion. Thereafter, the speed of the stirrer was lowered to 1000 RPM, and the continuous phase 2 was added to the emulsion, followed by interfacial polymerization at 80° C. for 12 hours to prepare a polyurethane microcapsule.

Comparative Example 5

The First Step 0.15 g of sodium dodecyl sulfate was dispersed in 59.85 g of distilled water to prepare a continuous phase 1. In addition, 1 g of polyvinyl alcohol was added to 9 g of distilled water and mixed to prepare a continuous phase 2.

The Second Step 0.5 g of sebacoyl chloride was added to 29.5 g of dodecane to prepare a dispersed phase.

The Third Step

Under the conditions of 2000 RPM, the dispersed phase was slowly added to the continuous phase 1 and stirred to prepare an emulsion. Thereafter, the speed of the stirrer was lowered to 1000 RPM, and the continuous phase 2 was added to the emulsion, followed by interfacial polymerization at 80° C. for 12 hours to prepare a polyurethane microcapsule.

Example 1

The First Step 1 g of silica was dispersed in 59 g of distilled water to prepare a continuous phase 1 (first solution). In addition, 1 g of polyethyleneimine was added to 9 g of distilled water to prepare a continuous phase 2 (second solution).

The Second Step 0.5 g of sebacoyl chloride was added to 29.5 g of dodecane to prepare a dispersed-phase solution.

The Third Step

Under the conditions of 2000 RPM, the dispersed-phase solution was slowly added to the continuous phase 1 (first solution) and stirred to prepare a pickering emulsion. Thereafter, the speed of the stirrer was lowered to 1000 RPM, and the continuous phase 2 (second solution) was added to the pickering emulsion, followed by interfacial polymerization at 80° C. for 12 hours to prepare an organic-inorganic hybrid microcapsule.

Example 12

The First Step 1 g of silica was dispersed in 59 g of distilled water to prepare a continuous phase 1 (first solution). In addition, 1 g of polyvinylalcohol was added to 9 g of distilled water to prepare a continuous phase 2 (second solution).

The Second Step 0.5 g of polyisocyanate was added to 29.5 g of dodecane to prepare a dispersed-phase solution.

The Third Step

Under the conditions of 2000 RPM, the dispersed-phase solution was slowly added to the continuous phase 1 (first solution) and stirred to prepare a pickering emulsion. Thereafter, the speed of the stirrer was lowered to 1000 RPM, and the continuous phase 2 (second solution) was added to the pickering emulsion, followed by interfacial polymerization at 80° C. for 12 hours to prepare an organic-inorganic hybrid microcapsule.

Example 13

The First Step 1 g of silica was dispersed in 59 g of distilled water to prepare a continuous phase 1 (first solution). In addition, 1 g of polyvinylalcohol was added to 9 g of distilled water to prepare a continuous phase 2 (second solution).

The Second Step 0.5 g of sebacoyl chloride was added to 29.5 g of dodecane to prepare a dispersed-phase solution.

The Third Step

Under the conditions of 2000 RPM, the dispersed-phase solution was slowly added to the continuous phase 1 (first solution) and stirred to prepare a pickering emulsion. Thereafter, the speed of the stirrer was lowered to 1000 RPM, and the continuous phase 2 (second solution) was added to the pickering emulsion, followed by interfacial polymerization at 80° C. for 12 hours to prepare an organic-inorganic hybrid microcapsule.

TABLE 3

|  | Comp. Ex. 3 | Comp. Ex. 4 | Comp. Ex. 5 | Ex. 11 | Ex. 12 | Ex. 13 |
|---|---|---|---|---|---|---|
| Distilled Water | 68.85 | 68.85 | 68.85 | 68 | 68 | 68 |
| Silica | — | — | — | 1 | 1 | 1 |
| Sodium dodecyl Sulfate | 0.15 | 0.15 | 0.15 | — | — | — |
| Polyisocyanate | — | 0.5 | — | — | 0.5 | — |
| Sebacoyl chloride | 0.5 | — | 0.5 | 0.5 | — | 0.5 |
| Polyethyleneimine | 1 | — | — | 1 | — | — |
| Polyvinylalcohol | — | 1 | 1 | — | 1 | 1 |
| Dodecane | 29.5 | 29.5 | 29.5 | 29.5 | 29.5 | 29.5 |
| Strength (MPa) | 421.9 | 637.5 | 511.4 | 53.1 | 75.2 | 49.8 |
| Size (μm) | 12.3 | 9.8 | 16.5 | 18.2 | 16.4 | 22.7 |

As shown in Table 2, the organic microcapsules of Comparative Examples 4 to 6 had too high strength, such as 421.9 to 637.5 MPa, even if the polymer materials were different. Thus, it was difficult to apply them to a product and strength control was also difficult.

On the other hand, the organic-inorganic hybrid microcapsules of Examples 10 to 13 of the present disclosure were similar in size, and had strength suitable for use in products of about 53.1 to 75.2 MPa by applying various polymer materials to silica (inorganic material). In addition, the above Examples showed an advantage of easy strength control, thereby improving processability and usability.

[Experimental Example 3] Strength Control of Capsules

Capsules of Examples 14 to 17 in which the polymer content was decreased or increased compared to Example 1 were prepared in the following manner, and the strength and size of each capsule were measured. The results are shown in Table 4. In addition, Examples 18 to 21 in which the polymer content was decreased or increased compared to Example 6 in which its composition of the dispersed-phase solution was changed were prepared, and the strength and size of each capsule were measured. The results are shown in Table 5.

Examples 14 to 17

The First Step 1 g of silica was dispersed in 59 g of distilled water to prepare a continuous phase 1 (first solution). In addition, polyethyleneimine was added to distilled water according to the contents disclosed in Table 4 to prepare a continuous phase 2 (second solution).

The Second Step

Polyisocyanate was added to dodecane to prepare a dispersed-phase solution.

The Third Step

Under the conditions of 2000 RPM, the dispersed-phase solution was slowly added to the continuous phase 1 (first solution) and stirred to prepare a pickering emulsion. Thereafter, the speed of the stirrer was lowered to 1000 RPM, and the continuous phase 2 (second solution) was added to the pickering emulsion, followed by interfacial polymerization at 80° C. for 12 hours to prepare an organic-inorganic hybrid microcapsule.

Examples 18 to 21

The First Step 1 g of silica was dispersed in 59 g of distilled water to prepare a continuous phase 1 (first solution). In addition, polyethyleneimine was added to distilled water according to the contents disclosed in Table 5 to prepare a continuous phase 2 (second solution).

The Second Step 0.5 g of 1,6-hexanediol diacrylate was added to 29.5 g of dodecane and mixed to prepare a dispersed-phase solution.

The Third Step

Under the conditions of 2000 RPM, the dispersed-phase solution was slowly added to the continuous phase 1 (first solution) and stirred to prepare a pickering emulsion. Thereafter, the speed of the stirrer was lowered to 1000 RPM, and the continuous phase 2 (second solution) was added to the pickering emulsion, followed by interfacial polymerization at 80° C. for 12 hours to prepare a biodegradable organic-inorganic hybrid microcapsule.

TABLE 4

|  | Ex. 14 | Ex. 15 | Ex. 1 | Ex. 16 | Ex. 17 |
|---|---|---|---|---|---|
| Distilled Water | 68.75 | 68.5 | 68.0 | 67.5 | 67.0 |
| Silica | 1 | 1 | 1 | 1 | 1 |
| Polyisocyanate | 0.125 | 0.25 | 0.5 | 0.75 | 1 |
| Polyethyleneimine | 0.25 | 0.5 | 1 | 1.5 | 2 |
| Dodecane | 29.875 | 29.75 | 29.5 | 29.25 | 29 |
| Strength (MPa) | 35.2 | 55.7 | 69.5 | 117.8 | 160.4 |
| Size (μm) | 36.1 | 24.8 | 18.2 | 16.6 | 12.4 |

TABLE 5

|  | Ex. 18 | Ex. 19 | Ex. 6 | Ex. 20 | Ex. 21 |
|---|---|---|---|---|---|
| Distilled Water | 68.75 | 68.5 | 68.0 | 67.5 | 67.0 |
| Silica | 1 | 1 | 1 | 1 | 1 |
| 1,6-Hexanediol diacrylate | 0.125 | 0.25 | 0.5 | 0.75 | 1 |

TABLE 5-continued

|  | Ex. 18 | Ex. 19 | Ex. 6 | Ex. 20 | Ex. 21 |
|---|---|---|---|---|---|
| Polyethyleneimine | 0.25 | 0.5 | 1 | 1.5 | 2 |
| Dodecane | 29.875 | 29.75 | 29.5 | 29.25 | 29 |
| Strength (MPa) | 31.1 | 53.4 | 65.7 | 109.3 | 155.9 |
| Size (μm) | 38.8 | 27.4 | 17.5 | 13.1 | 11.5 |

As shown in Tables 4 and 5, the present disclosure was able to control the strength of capsules according to the polymer content. In the case of Examples 16 to 17, it was confirmed that the strength of capsules became stronger as the contents of polyisocyanate and polyethyleneimine increased compared to Example 1.

In addition, in the case of Examples 20 to 21, it was confirmed that the strength of capsules was increased as the contents of 1,6-hexanediol diacrylate and polyethyleneimine increased compared to Example 6.

Accordingly, the present disclosure can provide a variety of organic-inorganic hybrid microcapsules capable of controlling the strength of capsules.

[Experimental Example 4] Release Behavior of Volatile Oil

After preparing the microcapsule of Comparative Example 5 in the following manner, the strength and size were measured, and the results are shown in Table 4.

In addition, with respect to Comparative Example 1, Comparative Example 5, Example 1, and Examples 9 to 12, the release behavior of volatile oil in the dispersed phase was compared.

As a method of measuring the release behavior of volatile oil, a mass change at 120° C. for 4 hours was measured using MA-100 manufactured by Satorius, and the results are shown in Tables 7 to 8 and FIGS. 3 to 4.

Comparative Example 6

The First Step
After treating the silica surface with 25% CTAC (Cetyltrimethyl ammonium chloride), it was dispersed in distilled water to prepare a continuous phase.

The Second Step
3 g of TEOS was added to 30 g of dodecane to prepare a dispersed phase.

The Third Step
Under the conditions of 2000 RPM, the dispersed phase was slowly added to the continuous phase and stirred to prepare a pickering emulsion. Thereafter, the pH of the emulsion was adjusted to 10 with NaOH, and interfacial polymerization was performed at 25° C. for 12 hours to prepare a silica-based microcapsule.

TABLE 6

|  | Comp. Ex. 6 |
|---|---|
| Distilled Water | 61 |
| Silica | 2 |
| 25% CTAC | 4 |
| TEOS | 3 |
| Dodecane | 30 |
| Strength (MPa) | 12.4 |
| Size (μm) | 36.1 |

TABLE 7

|  | Comp. Ex. 1 | Comp. Ex. 6 | Ex. 14 | Ex. 15 | Ex. 1 | Ex. 16 | Ex. 17 |
|---|---|---|---|---|---|---|---|
| Remaining amount after final drying (%) | 32.3 | 4.3 | 4.9 | 9.4 | 15.9 | 20.2 | 24.1 |

TABLE 8

|  | Comp. Ex. 2 | Comp. Ex. 6 | Ex. 18 | Ex. 19 | Ex. 6 | Ex. 20 | Ex. 21 |
|---|---|---|---|---|---|---|---|
| Remaining amount after final drying (%) | 33.5 | 4.3 | 4.6 | 8.8 | 16.3 | 21.5 | 26.4 |

As shown in Table 7 and FIG. 3, Examples 14 to 17 confirmed that the internal dispersed phase was gradually released over time. In addition, Examples 16 to 17 exhibited excellent sustained-release property overall, although the amount released was reduced as the contents of polyisocyanate and polyethyleneimine increased.

As shown in Table 8 and FIG. 4, Examples 18 to 21 confirmed that the internal dispersed phase was gradually released over time. In addition, Examples 20 and 21 exhibited excellent sustained-release property overall, although the amount released was reduced as the contents of 1,6-hexanediol diacrylate and polyethyleneimine increased.

[Experimental Example 5] Strength Comparison of Eco-Friendly Capsules to which Natural Polymer Materials are Applied Organic-inorganic hybrid capsules based on natural polymer materials were prepared in the following manner, and the strength and size of each capsule were measured. The strength of capsules was measured using a nanoindentation test device (CMS instrument). Herein, the strength was obtained by dividing the maximum load value by the contact area. The size of capsules was measured using Mastersizer 3000 manufactured by Malvern.

Comparative Example 7

The First Step
0.15 g of sodium dodecyl sulfate was dispersed in 59.85 g of distilled water to prepare a continuous phase 1. In addition, 1 g of chitosan was added to 9 g of distilled water to prepare a continuous phase 2.

The Second Step
0.5 g of polyisocyanate was added to 29.5 g of dodecane to prepare a dispersed phase.

The Third Step
Under the conditions of 2000 RPM, the dispersed phase was slowly added to the continuous phase 1 and stirred to prepare an emulsion. Thereafter, the speed of the stirrer was lowered to 1000 RPM, and the continuous phase 2 was added to the emulsion, followed by interfacial polymerization at 80° C. for 12 hours to prepare a polyurea microcapsule.

Comparative Example 8

The First Step
0.15 g of sodium dodecyl sulfate was dispersed in 59.85 g of distilled water to prepare a continuous phase 1. In addition, 1 g of chitosan was added to 9 g of distilled water to prepare a continuous phase 2.

The Second Step 0.5 g of sebacoyl chloride was added to 29.5 g of dodecane to prepare a dispersed phase.

The Third Step

Under the conditions of 2000 RPM, the dispersed phase was slowly added to the continuous phase 1 and stirred to prepare an emulsion. Thereafter, the speed of the stirrer was lowered to 1000 RPM, and the continuous phase 2 was added to the emulsion, followed by interfacial polymerization at 80° C. for 12 hours to prepare a polyurethane microcapsule.

Comparative Example 9

The First Step 0.15 g of sodium dodecyl sulfate was dispersed in 59.85 g of distilled water to prepare a continuous phase 1. In addition, 1 g of agarose was added to 9 g of distilled water to prepare a continuous phase 2.

The Second Step 0.5 g of polyisocyanate was added to 29.5 g of dodecane to prepare a dispersed phase.

The Third Step

Under the conditions of 2000 RPM, the dispersed phase was slowly added to the continuous phase 1 and stirred to prepare an emulsion. After lowering the speed of the stirrer to 1000 RPM, the continuous phase 2 was added to the emulsion, and a small amount of Tin dibutyl-diaurate was added thereto as a catalyst to increase reactivity. Then, interfacial polymerization was performed at 100° C. for 12 hours to prepare an agarose-based polyurethane microcapsule.

Comparative Example 10

The First Step 0.15 g of sodium dodecyl sulfate was dispersed in 59.85 g of distilled water to prepare a continuous phase 1. In addition, 1 g of agarose was added to 9 g of distilled water to prepare a continuous phase 2.

The Second Step 0.5 g of sebacoyl chloride was added to 29.5 g of dodecane to prepare a dispersed phase.

The Third Step

Under the conditions of 2000 RPM, the dispersed phase was slowly added to the continuous phase 1 and stirred to prepare an emulsion. Thereafter, the speed of the stirrer was lowered to 1000 RPM, and the continuous phase 2 was added to the emulsion, followed by interfacial polymerization at 80° C. for 12 hours to prepare an agarose-based polyester microcapsule.

Example 22

The First Step 1 g of silica was dispersed in 59 g of distilled water to prepare a continuous phase 1 (first solution). In addition, 1 g of chitosan was added to 9 g of distilled water to prepare a continuous phase 2 (second solution).

The Second Step 0.5 g of polyisocyanate was added to 29.5 g of dodecane to prepare a dispersed-phase solution.

The Third Step

Under the conditions of 2000 RPM, the dispersed-phase solution was slowly added to the continuous phase 1 (first solution) and stirred to prepare a pickering emulsion. Thereafter, the speed of the stirrer was lowered to 1000 RPM, and the continuous phase 2 (second solution) was added to the pickering emulsion, followed by interfacial polymerization at 80° C. for 12 hours to prepare an eco-friendly organic-inorganic hybrid microcapsule.

Example 23

The First Step 1 g of silica was dispersed in 59 g of distilled water to prepare a continuous phase 1 (first solution). In addition, 1 g of chitosan was added to 9 g of distilled water to prepare a continuous phase 2 (second solution).

The Second Step 0.5 g of sebacoyl chloride was added to 29.5 g of dodecane to prepare a dispersed-phase solution.

The Third Step

Under the conditions of 2000 RPM, the dispersed-phase solution was slowly added to the continuous phase 1 (first solution) and stirred to prepare a pickering emulsion. Thereafter, the speed of the stirrer was lowered to 1000 RPM, and the continuous phase 2 (second solution) was added to the pickering emulsion, followed by interfacial polymerization at 80° C. for 12 hours to prepare an eco-friendly organic-inorganic hybrid microcapsule.

Example 24

The First Step 1 g of silica was dispersed in 59 g of distilled water to prepare a continuous phase 1 (first solution). In addition, 1 g of agarose was added to 9 g of distilled water to prepare a continuous phase 2 (second solution).

The Second Step 0.5 g of polyisocyanate was added to 29.5 g of dodecane to prepare a dispersed-phase solution.

The Third Step

Under the conditions of 2000 RPM, the dispersed-phase solution was slowly added to the continuous phase 1 (first solution) and stirred to prepare a pickering emulsion. After lowering the speed of the stirrer to 1000 RPM, the continuous phase 2 (second solution) was added to the pickering emulsion, and a small amount of Tin dibutyl-diaurate was added thereto as a catalyst to increase reactivity. Then, interfacial polymerization was performed at 100° C. for 12 hours to prepare an eco-friendly organic-inorganic hybrid microcapsule.

Example 25

The First Step 1 g of silica was dispersed in 59 g of distilled water to prepare a continuous phase 1 (first solution). In addition, 1 g of agarose was added to 9 g of distilled water to prepare a continuous phase 2 (second solution).

The Second Step 0.5 g of sebacoyl chloride was added to 29.5 g of dodecane to prepare a dispersed-phase solution.

The Third Step

Under the conditions of 2000 RPM, the dispersed-phase solution was slowly added to the continuous phase 1 (first solution) and stirred to prepare a pickering emulsion. Thereafter, the speed of the stirrer was lowered to 1000 RPM, and the continuous phase 2 (second solution) was added to the pickering emulsion, followed by interfacial polymerization at 80° C. for 12 hours to prepare an eco-friendly organic-inorganic hybrid microcapsule.

TABLE 9

|  | Comp. Ex. 7 | Comp. Ex. 8 | Comp. Ex. 9 | Comp. Ex. 10 | Ex. 22 | Ex. 23 | Ex. 24 | Ex. 25 |
|---|---|---|---|---|---|---|---|---|
| Distilled Water | 68.85 | 68.85 | 68.85 | 68.85 | 68 | 68 | 68 | 68 |
| Silica | — | — | — | — | 1 | 1 | 1 | 1 |
| Sodium dodecyl Sulfate | 0.15 | 0.15 | 0.15 | 0.15 | — | — | — | — |
| Polyisocyanate | 0.5 | — | 0.5 | — | 0.5 | — | 0.5 | — |
| Sebacoyl chloride | — | 0.5 | — | 0.5 | — | 0.5 | — | 0.5 |
| Chitosan | 1 | 1 | — | — | 1 | 1 | — | — |
| Agarose | — | — | 1 | 1 | — | — | 1 | 1 |
| Dodecane | 29.5 | 29.5 | 29.5 | 29.5 | 29.5 | 29.5 | 29.5 | 29.5 |
| Strength (MPa) | 499.5 | 384.4 | 436.1 | 488.4 | 60.3 | 49.5 | 65.9 | 45.1 |
| Size (μm) | 14.7 | 16.5 | 18.9 | 17.9 | 19.5 | 22.1 | 23.4 | 25.4 |

[Experimental Example 6] Preparation of Fragrance Capsule and Laundry Evaluation 1

After preparing each fragrance capsule of Comparative Examples and Examples as an actual application example in the following manner, the strength and size were measured, and laundry evaluation was also conducted.

That is, it was thought that the organic-inorganic hybrid capsules of Examples would give off a scent well, because they are excellent in expressing the active ingredient and have excellent fracturability. To verify this, 5 Comparative Examples and 2 Examples were prepared, and their strength was measured, followed by laundry evaluation.

Commercially available oil was used for the fragrance oil. In addition, previously known polyurea, polyamide, polyurethane, polyester, and melamine-formaldehyde resin capsules were set as Comparative Examples 11 to 15.

1) Strength and Size:
They were measured according to the method described above.

2) Laundry Evaluation
The evaluation fiber was prepared by using a commercially available cotton towel (30×20 cm), and the cotton towel was washed five times with a washing machine using general laundry detergent in a standard amount, followed by dehydration. Each microcapsule prepared in the above Comparative Examples and Examples was made into a 1% aqueous solution, and then quantified to have a standard usage amount (0.67 MO L washing water) and put in a stirring washing machine. Thereafter, the cotton towel was treated with a rinse course, and taken out after dehydration. Then, the cotton towel was dried for 12 hours at a humidity of 30% and a temperature of 25° C.

20 experienced panelists performed a sensory evaluation test three times (immediately after washing, after drying, after rubbing) to evaluate the fragrance intensity. The fragrance intensity was given from the lowest point 0 (capsule-free cotton towel) to the highest point 5, and the test was repeated three times or more to obtain an average value, which was used to evaluate the residual scent. The results are shown in Table 8 and FIG. 4.

Comparative Example 11

The First Step
0.15 g of sodium dodecyl sulfate was dispersed in 59.85 g of distilled water to prepare a continuous phase 1. In addition, 1 g of polyethyleneimine was added to 9 g of distilled water to prepare a continuous phase 2.

The Second Step
0.5 g of polyisocyanate was added to 29.5 g of fragrance to prepare a dispersed phase.

The Third Step
Under the conditions of 2000 RPM, the dispersed phase was slowly added to the continuous phase 1 and stirred to prepare an emulsion. Thereafter, the speed of the stirrer was lowered to 1000 RPM, and the continuous phase 2 was added to the emulsion, followed by interfacial polymerization at 80° C. for 12 hours to prepare a polyurea microcapsule.

Comparative Example 12

The First Step
0.15 g of sodium dodecyl sulfate was dispersed in 59.85 g of distilled water to prepare a continuous phase 1. In addition, 1 g of polyethyleneimine was added to 9 g of distilled water to prepare a continuous phase 2.

The Second Step
0.5 g of sebacoyl chloride was added to 29.5 g of fragrance to prepare a dispersed phase.

The Third Step
Under the conditions of 2000 RPM, the dispersed phase was slowly added to the continuous phase 1 and stirred to prepare an emulsion. Thereafter, the speed of the stirrer was lowered to 1000 RPM, and the continuous phase 2 was added to the emulsion, followed by interfacial polymerization at 80° C. for 12 hours to prepare a polyamide microcapsule.

Comparative Example 13

The First Step
0.15 g of sodium dodecyl sulfate was dispersed in 59.85 g of distilled water to prepare a continuous phase 1. In addition, 1 g of polyvinyl alcohol was added to 9 g of distilled water to prepare a continuous phase 2.

The Second Step
0.5 g of polyisocyanate was added to 29.5 g of fragrance to prepare a dispersed phase.

The Third Step
Under the conditions of 2000 RPM, the dispersed phase was slowly added to the continuous phase 1 and stirred to prepare an emulsion. After lowering the speed of the stirrer to 1000 RPM, the continuous phase 2 was added to the emulsion, and a small amount of Tin dibutyl-diaurate was added thereto as a catalyst to increase reactivity. Then, interfacial polymerization was performed at 100° C. for 12 hours to prepare a polyurethane microcapsule.

Comparative Example 14

The First Step
0.15 g of sodium dodecyl sulfate was dispersed in 59.85 g of distilled water to prepare a continuous phase 1. In addition, 1 g of polyvinyl alcohol was added to 9 g of distilled water to prepare a continuous phase 2.

The Second Step 0.5 g of sebacoyl chloride was added to 29.5 g of fragrance to prepare a dispersed phase.

The Third Step

Under the conditions of 2000 RPM, the dispersed phase was slowly added to the continuous phase 1 and stirred to prepare an emulsion. Thereafter, the speed of the stirrer was lowered to 1000 RPM, and the continuous phase 2 was added to the emulsion, followed by interfacial polymerization at 80° C. for 12 hours to prepare a polyester microcapsule.

Comparative Example 15

The First Step

Sodium dodecyl sulfate, Tween 20, gum arabic, and pre-melamine formaldehyde solution were dispersed in 54 g of distilled water to prepare a continuous phase.

The Second Step

Under the conditions of 2000 RPM, 30 g of fragrance (dispersed phase) was gradually added to the continuous phase to prepare an emulsion.

The Third Step

After lowering the speed of the stirrer to 1000 RPM, the pH was lowered to 5 with citric acid, and a reaction for forming a capsule was performed at 70° C. for 3 hours. After terminating the reaction by adjusting the pH to 7.5 with tromethamine, a melamine-formaldehyde resin capsule was prepared.

Example 26

The First Step 1 g of silica was dispersed in 59 g of distilled water to prepare a continuous phase 1 (first solution). In addition, 1 g of polyethyleneimine was added to 9 g of distilled water to prepare a continuous phase 2 (second solution).

The Second Step 0.5 g of polyisocyanate was added to 29.5 g of fragrance to prepare a dispersed-phase solution.

The Third Step

Under the conditions of 2000 RPM, the dispersed-phase solution was slowly added to the continuous phase 1 (first solution) and stirred to prepare a pickering emulsion. Thereafter, the speed of the stirrer was lowered to 1000 RPM, and the continuous phase 2 (first solution) was added to the pickering emulsion, followed by interfacial polymerization at 80° C. for 12 hours to prepare an eco-friendly organic-inorganic hybrid microcapsule.

Example 27

The First Step 1 g of silica was dispersed in 59 g of distilled water to prepare a continuous phase 1 (first solution). In addition, 1 g of chitosan was added to 9 g of distilled water to prepare a continuous phase 2 (second solution).

The Second Step 0.5 g of polyisocyanate was added to 29.5 g of fragrance to prepare a dispersed-phase solution.

The Third Step

Under the conditions of 2000 RPM, the dispersed-phase solution was slowly added to the continuous phase 1 (first solution) and stirred to prepare a pickering emulsion. Thereafter, the speed of the stirrer was lowered to 1000 RPM, and the continuous phase 2 (second solution) was added to the pickering emulsion, followed by interfacial polymerization at 80° C. for 12 hours to prepare an eco-friendly organic-inorganic hybrid microcapsule.

TABLE 10

| | Comp. Ex. 11 | Comp. Ex. 12 | Comp. Ex. 13 | Comp. Ex. 14 | Comp. Ex. 15 | Ex. 26 | Ex. 27 |
|---|---|---|---|---|---|---|---|
| Distilled Water | 68.85 | 68.85 | 68.85 | 68.85 | 54 | 68 | 68 |
| Silica | — | — | — | — | — | 1 | 1 |
| Sodium dodecyl Sulfate | 0.15 | 0.15 | 0.15 | 0.15 | 0.5 | — | — |
| Polyisocyanate | 0.5 | — | 0.5 | — | — | 0.5 | 0.5 |
| Sebacoyl chloride | — | 0.5 | — | 0.5 | — | — | — |
| Polyethyleneimine | 1 | 1 | — | — | — | 1 | — |
| Chitosan | — | — | — | — | — | — | 1 |
| Polyvinylalcohol | — | — | 1 | 1 | — | — | — |
| Tween 20 | — | — | — | — | 2 | — | — |
| Arabic gum | — | — | — | — | 5 | — | — |
| Pre-melamine formaldehyde Solution | — | — | — | — | 7.5 | — | — |
| Tromethamine | — | — | — | — | 0.5 | — | — |
| Citric acid | — | — | — | — | 0.5 | — | — |
| Fragrance | 29.5 | 29.5 | 29.5 | 29.5 | 30 | 29.5 | 29.5 |
| Strength (MPa) | 421.9 | 637.5 | 511.4 | 553.2 | 317.6 | 53.1 | 50.9 |
| Size (μm) | 12.3 | 9.8 | 16.5 | 16.5 | 7.7 | 18.2 | 20.6 |

As shown in Table 10, eco-friendly organic-inorganic hybrid microcapsules were prepared using various natural polymer materials. Although they were similar in size, they had lower strength compared to Comparative Examples 11 to 15.

TABLE 11

| | Comp. Ex. 11 | Comp. Ex. 12 | Comp. Ex. 13 | Comp. Ex. 14 | Comp. Ex. 15 | Ex. 26 | Ex. 27 |
|---|---|---|---|---|---|---|---|
| Immediately after washing | 0.74 | 0.54 | 0.99 | 0.87 | 1.07 | 3.3 | 3.11 |
| After drying | 0.86 | 0.23 | 0.42 | 1.12 | 1.25 | 3.55 | 2.94 |
| After rubbing | 1.11 | 0.67 | 1.43 | 1.21 | 2.34 | 4.65 | 3.87 |

As shown in Table 11 and FIG. 5, it was confirmed that Example 26 of the present disclosure gave off a scent better than Comparative Examples 10 to 15 in laundry evaluation. In addition, Example 27 using a natural polymer also gave off a scent better than Comparative Examples 11 to 15 in laundry evaluation.

[Experimental Example 7] Preparation of Fragrance Capsule and Laundry Evaluation 2

Fragrance capsules of Comparative Examples and Example were prepared with a different composition of the dispersed phase, and compared as in Experimental Example 6.

That is, after preparing each fragrance capsule of Comparative Examples 16 to 17 and Example 28 as an actual application example in the following manner, the strength and size were measured, and laundry evaluation was also conducted.

That is, it was thought that the biodegradable organic-inorganic hybrid capsule of Example would give off a scent well, because it is excellent in expressing the active ingredient and has excellent fracturability. To verify this, 2 Comparative Examples and 1 Example were prepared, and their strength was measured, followed by laundry evaluation.

Commercially available oil was used for the fragrance oil. In addition, previously known polyurea, polyamide, polyurethane, polyester, and melamine-formaldehyde resin capsules were set as Comparative Examples 16 to 17.

1) Strength and Size:

They were measured according to the method described above.

2) Laundry Evaluation

The evaluation fiber was prepared by using a commercially available cotton towel (30×20 cm), and the cotton towel was washed five times with a washing machine using general laundry detergent in a standard amount, followed by dehydration. Each microcapsule prepared in the above Comparative Examples and Examples was made into a 1% aqueous solution, and then quantified to have a standard usage amount (0.67 ml/1 L washing water) and put in a stirring washing machine. Thereafter, the cotton towel was treated with a rinse course, and taken out after dehydration. Then, the cotton towel was dried for 12 hours at a humidity of 30% and a temperature of 25° C.

20 experienced panelists performed a sensory evaluation test three times (immediately after washing, after drying, after rubbing) to evaluate the fragrance intensity. The fragrance intensity was given from the lowest point 0 (capsule-free cotton towel) to the highest point 5, and the test was repeated three times or more to obtain an average value, which was used to evaluate the residual scent. The results are shown in Table 5 and FIG. 4.

Comparative Example 16

The First Step 0.15 g of sodium dodecyl sulfate was dispersed in 59.85 g of distilled water to prepare a continuous phase 1 (first solution). In addition, 1 g of polyethyleneimine was added to 9 g of distilled water to prepare a continuous phase 2 (second solution).

The Second Step 0.5 g of 1,6-hexanediol diacrylate was added to 29.5 g of fragrance to prepare a dispersed phase.

The Third Step

Under the conditions of 2000 RPM, the dispersed phase was slowly added to the continuous phase 1 (first solution) and stirred to prepare an emulsion. Thereafter, the speed of the stirrer was lowered to 1000 RPM, and the continuous phase 2 (second solution) was added to the emulsion, followed by interfacial polymerization at 80° C. for 12 hours to prepare a poly($\beta$-amino ester) microcapsule.

Comparative Example 17

The First Step

Sodium dodecyl sulfate, Tween 20, gum arabic, and pre-melamine formaldehyde solution were dispersed in 54 g of distilled water to prepare a continuous phase.

The Second Step

Under the conditions of 2000 RPM, 30 g of fragrance (dispersed phase) was gradually added to the continuous phase to prepare an emulsion.

The Third Step

After lowering the speed of the stirrer to 1000 RPM, the pH was lowered to 5 with citric acid, and a reaction for forming a capsule was performed at 70° C. for 3 hours. After terminating the reaction by adjusting the pH to 7.5 with tromethamine, a melamine-formaldehyde resin capsule was prepared.

Example 28

The First Step 1 g of silica was dispersed in 59 g of distilled water to prepare a continuous phase 1 (first solution). In addition, 1 g of polyethyleneimine was added to 9 g of distilled water to prepare a continuous phase 2 (second solution).

The Second Step 0.5 g of 1,6-hexanediol diacrylate was added to 29.5 g of fragrance to prepare a dispersed-phase solution.

The Third Step

Under the conditions of 2000 RPM, the dispersed-phase solution was slowly added to the continuous phase 1 (first solution) and stirred to prepare a pickering emulsion. Thereafter, the speed of the stirrer was lowered to 1000 RPM, and the continuous phase 2 (second solution) was added to the pickering emulsion, followed by interfacial polymerization at 80° C. for 12 hours to prepare a biodegradable organic-inorganic hybrid microcapsule.

TABLE 12

|  | Comp. Ex. 16 | Comp. Ex. 17 | Comp. Ex. 28 |
|---|---|---|---|
| Immediately after washing | 0.97 | 1.07 | 3.15 |
| After drying | 1.34 | 1.25 | 3.88 |
| After rubbing | 1.91 | 2.34 | 4.47 |

As shown in Table 12 and FIG. 6, it was confirmed that Example 28 of the present disclosure gave off a scent better than Comparative Examples 16 to 17 in laundry evaluation.

[Experimental Example 8] Biodegradability Evaluation of Fragrance Capsules

In this experimental example, Example 29 was prepared in the following manner. Thereafter, the outer wall material of the fragrance capsule of the present disclosure was separated, and the biodegradability of Comparative Example 17 and Examples 28 to 29 was evaluated and compared.

TABLE 13

|  | Ex. 29 |
|---|---|
| Distilled Water | 68 |
| Silica | 1 |
| 1,6-Hexanediol diacrylate | 0.5 |
| Chitosan | 1 |
| Fragrance | 29.5 |
| Strength (MPa) | 50.1 |
| Size (μm) | 20.4 |

Example 29

The First Step 1 g of silica was dispersed in 59 g of distilled water to prepare a continuous phase 1. In addition, 1 g of chitosan was added to 9 g of distilled water to prepare a continuous phase 2.

The Second Step 0.5 g of 1,6-hexanediol diacrylate was added to 29.5 g of fragrance to prepare a dispersed phase.

The Third Step

Under the conditions of 2000 RPM, the dispersed phase was slowly added to the continuous phase 1 and stirred to prepare a pickering emulsion. Thereafter, the speed of the stirrer was lowered to 1000 RPM, and the continuous phase 2 was added to the pickering emulsion, followed by interfacial polymerization at 80° C. for 12 hours to prepare a biodegradable organic-inorganic hybrid microcapsule.

Separation of Outer Wall Material

First, the outer wall material of the capsule and the core oil (fragrance oil) were separated. The composition of the present disclosure (Comparative Example 17, Examples 28 and 29) was first dispersed in ethanol, and then only the outer wall material of the capsule was separated using a centrifuge. Thereafter, the core oil (fragrance oil) was removed with ethanol three times more in the same manner, and the outer wall material was dried at 60° C. for 24 h with a vacuum pump.

Measurement of Biodegradability

The biodegradability was measured according to the well-known OECD 301 F method by measuring COD (Chemical Oxygen Demand) and BOD (Biochemical Oxygen Demand), and then calculating the biodegradability in the following manner.

COD was measured according to the ISO 6060 method. Briefly, an appropriate amount of a sample was oxidized with sulfuric acid and an excess of potassium dichromate, and the remaining potassium dichromate was titrated using FAS (Ferrous ammonium sulfate). Thereafter, COD was calculated from the number of moles of dichromate used in the oxidation reaction.

For measuring BOD, an aqueous solution containing microorganisms was prepared according to the method specified in OECD 301, and an appropriate amount of sample (0.1 g or more per liter) was added thereto to measure oxygen consumption with a respirometer for 28 days. Herein, a potassium hydroxide solution was used to remove carbon dioxide generated by microorganisms, a blank solution without a sample was simultaneously measured, and BOD was calculated by the following Equation 1.

$$BOD = \frac{\text{Amount of oxygen consumed in the decomposition process of sample (mg)} - \text{Amount of oxygen consumed in blank (mg)}}{\text{Amount of sample used (mg)}} \quad [\text{Equation 1}]$$

The biodegradability was obtained by the following Equation 2.

$$\text{Biodegradability (\%)} = \frac{BOD}{COD} \times 100 \quad [\text{Equation 2}]$$

TABLE 14

|  | Comp. Ex. 17 | Comp. Ex. 28 | Comp. Ex. 29 |
|---|---|---|---|
| Biodegradability (%) | 10.4 | 62.9 | 86.2 |

As shown in Table 14, Example 28 of the present disclosure exhibited better biodegradability than Comparative Example 17. In addition, it was confirmed that Example 29 using a natural polymer exhibited better biodegradability than Example 28.

The invention claimed is:

1. A method for preparing an organic-inorganic hybrid microcapsule comprising the steps of:
    a first step of preparing a first continuous-phase solution containing inorganic nanoparticles and a second continuous-phase solution containing a polymer precursor 1 for reinforcing an outer wall;
    a second step of preparing a dispersed-phase solution containing a polymer precursor 2 which reacts with the polymer precursor 1 or containing an active ingredient and the polymer precursor 2; and
    a third step of forming a picketing emulsion by adding the dispersed-phase solution to the first solution, and then forming an outer wall of the capsule through interfacial polymerization by adding the second solution,
    wherein the outer wall of the capsule comprises i) at least one polymer selected from the group consisting of polyamide, polyurethane, polyurea, polyester and poly(β-amino ester), and ii) inorganic nanoparticles; and
    the polymer precursor 1 for reinforcing the outer wall and the polymer precursor 2 each independently contain at least one precursor for forming a polymer selected from the group consisting of polyamide, polyurethane, polyurea, polyester, and poly(β-amino ester),
    wherein the polymer precursor 2 is at least one selected from the group consisting of a compound containing two or more acid chloride structures represented by the Chemical Formula 3, and a compound containing two or more chloroformate structures represented by the following Chemical Formula 5:

[Chemical Formula 3]

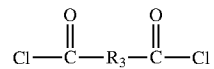

(in Chemical Formula 3, each $R_3$ may independently comprise C1 to C50 alkylene, a C3 to C60 cyclic hydrocarbon group, or C1 to C50 alkylene and a C3 to C60 cyclic hydrocarbon group having or not having at least one acid chloride (-COCl) or at least one heteroatom)

[Chemical Formula 5]

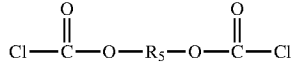

(in Chemical Formula 5, each $R_5$ may independently comprise C1 to C50 alkylene, a C3 to C60 cyclic hydrocarbon group, or C1 to C50 alkylene and a C3 to C60 cyclic hydrocarbon group having or not having at least one chloroformate (-OCOCl) or at least one heteroatom).

2. The method for preparing an organic-inorganic hybrid microcapsule of claim 1, wherein the polymer precursor 1 is at least one selected from the group consisting of a compound having two or more amine groups represented by the following Chemical Formula 1, a compound having two or more hydroxyl groups represented by the following Chemical Formula 2, and a natural polymer:

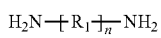

[Chemical Formula 1]

(in Chemical Formula 1, each $R_1$ may independently comprise C1 to C50 alkylene, a C3 to C60 cyclic hydrocarbon group, or C1 to C50 alkylene and a C3 to C60 cyclic hydrocarbon group having or not having at least one amine group or at least one heteroatom, and n is an integer of 1 to 5000)

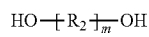

[Chemical Formula 2]

(in Chemical Formula 2, each $R_2$ may independently comprise C1 to C50 alkylene, a C3 to C60 cyclic hydrocarbon group, or C1 to C50 alkylene and a C3 to C60 cyclic hydrocarbon group having or not having at least one hydroxyl group or at least one heteroatom, and m is an integer of 1 to 5000).

3. The method for preparing an organic-inorganic hybrid microcapsule of claim 2, wherein the compound having two or more amine groups is at least one selected from the group consisting of m ethylenedi amine, ethylenediamine, diethylenetriamine, triethylenetetramine, tetraethylenepentamine, tris(2-aminoethyl)amine, polyethyleneimine, poly(propylene glycol) bis(2-aminopropyl ether), trimethylolpropane tris[poly(propylene glycol), amine terminated] ether, polyethylene glycol) bis(amine), o-phenylenediamine, p-phenylenediamine, m-phenylenediamine, 2,4-diaminotoluene, 2,3-diaminotoluene, 2, 5-diaminotoluene, 3,3'diaminodiphenylmethane, 3,4'-diaminodiphenylmethane, 4,4'-diaminodiphenylmethane, 4,4'-ethylenedianiline, 4,4'-diaminodiphenyl sulfide, 4,4'-oxydianiline, pararosaniline base, melamine and tetrakis(4-aminophenyl)methane).

4. The method for preparing an organic-inorganic hybrid microcapsule of claim 2, wherein the natural polymer is at least one selected from the group consisting of gelatin, chitosan, polylysine, gum arabic, polysaccharides, pectin, and alginate.

5. The method for preparing a biodegradable organic-inorganic hybrid microcapsule of claim 1, wherein the polymer precursor 2 is a compound containing two or more acrylate structures represented by the following Chemical Formula 6:

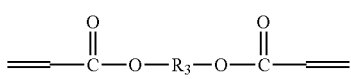

[Chemical Formula 6]

(in Chemical Formula 6, each $R_3$ may independently comprise C1 to C50 alkylene, a C3 to C60 cyclic hydrocarbon group, or C1 to C50 alkylene and a C3 to C60 cyclic hydrocarbon group having or not having at least one acrylate or at least one heteroatom).

6. The method for preparing an organic-inorganic hybrid microcapsule of claim 1, wherein the inorganic nanoparticles are contained in an amount of 0001 to 30 wt % based on a total weight of the first continuous-phase solution.

7. The method for preparing an organic-inorganic hybrid microcapsule of claim 1, wherein the polymer precursor 1 is contained in an amount of 0,001 to 20 wt % based on a total weight of the second continuous-phase solution.

8. The method for preparing an organic-inorganic hybrid microcapsule of claim 1, wherein the polymer precursor 2 is contained in an amount of 0.001 to 30 wt % based on a total weight of the dispersed-phase solution.

9. The method for preparing an organic-inorganic hybrid microcapsule of claim 1, wherein the dispersed-phase solution further comprises at least one solvent selected from the group consisting of pentane, hexane, cyclohexane, heptane, octane, isododecane, dodecane, ethyl ether, butyl ether, methyl-t-butyl ether, ethyl acetate, butyl acetate, ethyl butyrate, methyl ethyl ketone, benzene, toluene, xylene, dichloromethane, dichloroethane, chloroform, carbon tetrachloride, dimethicone, and cyclomethicone.

10. The method for preparing an organic-inorganic hybrid microcapsule of claim 1, wherein the inorganic nanoparticles are at least one selected from the group consisting of halloysite nanotuhes, laponite, kaolinite clay, colloidal silica, calcium hydroxide, magnesium hydroxide, magnesium oxide, alumina, aluminum hydroxide, aluminum phosphate, calcium pyrrolate, aluminum pyrrolate, and zinc pyrrolate.

11. The method for preparing an organic-inorganic hybrid microcapsule of claim 1, wherein the active ingredient is at least one selected from the group consisting of fragrance, dye, catalyst, antioxidant, and drug.

12. An organic-inorganic hybrid microcapsule, comprising a dispersed phase which is a core, and a hybrid capsule outer wall formed at an interface of the dispersed phase and surrounding outside of the dispersed phase;

wherein the hybrid capsule outer wall is an inorganic nanoparticles-polymer resin composite containing i) at least one polymer selected from the group consisting of polyamides polyurethane, polyurea, polyester and poly (β-amino ester), and ii) inorganic nanoparticles, wherein the polymer precursor 2 is at least one selected from the group consisting of a compound containing two or more acid chloride structures represented by the Chemical Formula 3, and a compound containing two or more chloroformate structures represented by the following Chemical Formula 5:

[Chemical Formula 3]

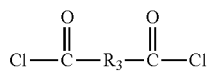

(in Chemical Formula 3, each $R_3$ may independently comprise C1 to C50 alkylene, a C3 to C60 cyclic hydrocarbon group, or C1 to C50 alkylene and a C3 to C60 cyclic hydrocarbon group having or not having at least one acid chloride (-COCl) or at least one heteroatom)

[Chemical Formula 5]

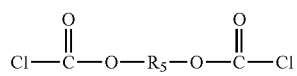

(in Chemical Formula 5, each $R_5$ may independently comprise C1 to C50 alkylene, a C3 to C60 cyclic hydrocarbon group or C1 to C50 alkylene and a C3 to C60 cyclic hydrocarbon group having or not having at least one chloroformate (-OCOCl) or at least one heteroatom).

13. The organic-inorganic hybrid microcapsule of claim 12, wherein the dispersed phase is contained in an amount of 1 to 90 wt % based on a total weight of the microcapsule.

14. The organic-inorganic hybrid microcapsule of claim 12, wherein the microcapsule has strength of 40 to 200 MPa.

15. The organic-inorganic hybrid microcapsule of claim 12, wherein an average particle diameter is 0.1 μm or more and 1000 μm or less.

\* \* \* \* \*